(12) United States Patent
Hickey et al.

(10) Patent No.: US 8,338,646 B2
(45) Date of Patent: Dec. 25, 2012

(54) MODAFINIL COMPOSITIONS

(75) Inventors: Magali Bourghol Hickey, Medford, MA (US); Matthew Peterson, Hopkinton, MA (US); Orn Almarsson, Shrewsbury, MA (US); Mark Oliveira, Framingham, MA (US)

(73) Assignee: Cephalon, Inc, Frazer, PA (US)

( * ) Notice: Subject to any disclaimer, the term of this patent is extended or adjusted under 35 U.S.C. 154(b) by 341 days.

(21) Appl. No.: 12/708,998

(22) Filed: Feb. 19, 2010

(65) Prior Publication Data

US 2010/0210731 A1    Aug. 19, 2010

Related U.S. Application Data

(63) Continuation of application No. 10/587,086, filed as application No. PCT/US2005/002782 on Feb. 1, 2005, now abandoned.

(60) Provisional application No. 60/542,752, filed on Feb. 6, 2004, provisional application No. 60/560,411, filed on Apr. 6, 2004, provisional application No. 60/573,412, filed on May 21, 2004, provisional application No. 60/579,176, filed on Jun. 12, 2004, provisional application No. 60/581,992, filed on Jun. 22, 2004, provisional application No. 60/586,752, filed on Jul. 9, 2004, provisional application No. 60/588,236, filed on Jul. 15, 2004, provisional application No. 60/631,786, filed on Nov. 30, 2004.

(30) Foreign Application Priority Data

Sep. 4, 2004    (WO) ................ PCT/US2004/029013

(51) Int. Cl.
*C07C 233/65* (2006.01)

(52) U.S. Cl. ........................................ 564/162; 514/618
(58) Field of Classification Search .................. 564/162; 514/618

See application file for complete search history.

(56) References Cited

U.S. PATENT DOCUMENTS

| 4,927,855 | A | 5/1990 | Lafon |
| 6,992,219 | B2 | 1/2006 | Broquaire et al. |
| 7,405,323 | B2 | 7/2008 | Broquaire et al. |
| 8,048,222 | B2 * | 11/2011 | Ceausu et al. .................. 117/68 |
| 2002/0043207 | A1 | 4/2002 | Singer et al. |
| 2003/0224006 | A1 | 12/2003 | Zaworotko et al. |
| 2004/0019211 | A1 | 1/2004 | Remenar |
| 2004/0102523 | A1 | 5/2004 | Broquaire et al. |
| 2005/0034652 | A1 | 2/2005 | Ceausu et al. |
| 2006/0135621 | A1 | 6/2006 | Neckebrock et al. |

FOREIGN PATENT DOCUMENTS

| FR | 2849029 | 6/2004 |
| WO | WO 02/10125 | 2/2002 |
| WO | WO 02/056915 | 7/2002 |
| WO | WO 03/074474 | 9/2003 |

OTHER PUBLICATIONS

Osorio-Lozada et al., Tetrahedron: Asymmetry, 2004, vol. 15, No. 23 pp. 3811-3815.
Database CAPLUS on STN, Acct. No. 2002:107306, Singer et al., WO2002010125 (Feb. 7, 2002) (abstract).
FDA Approved Labeling Text for NDA 20-717/S-005 & S-008 Approved Jan. 23, 2004, pp. 1-35.

* cited by examiner

*Primary Examiner* — Shailendra Kumar

(57)    ABSTRACT

Polymorphs and solvates of racemic, enantiomerically pure, and enantiomerically mixed modafinil are formed and discussed. In addition, said forms are described as useful for the treatment of many conditions including, but not limited to, narcolepsy.

4 Claims, 23 Drawing Sheets

MODAFINIL COMPOSITIONS

CROSS REFERENCE TO RELATED APPLICATIONS

This application is a continuation of U.S. application Ser. No. 10/587,086, filed Jul. 21, 2006, now abandoned which was the National Stage of International Application No. PCT/US2005/02782, filed Feb. 1, 2005, which claims the benefit of PCT/US2004/029013, filed Sep. 4, 2004, U.S. Provisional Application No. 60/542,752, filed Feb. 6, 2004, U.S. Provisional Application No. 60/560,411, filed Apr. 6, 2004, U.S. Provisional Application No. 60/573,412, filed May 21, 2004, U.S. Provisional Application No. 60/579,176, filed Jun. 12, 2004, U.S. Provisional Application No. 60/581,992, filed Jun. 22, 2004, U.S. Provisional Application No. 60/586,752, filed Jul. 9, 2004, U.S. Provisional Application No. 60/588,236, filed Jul. 15, 2004, and U.S. Provisional Application No. 60/631,786, filed Nov. 30, 2004.

FIELD OF THE INVENTION

The present invention relates to modafinil-containing compositions, pharmaceutical compositions comprising modafinil, and methods for preparing the same.

BACKGROUND OF THE INVENTION

Active pharmaceutical ingredients (API or APIs (plural)) in pharmaceutical compositions can be prepared in a variety of different forms. Such APIs can be prepared so as to have a variety of different chemical forms including chemical derivatives, solvates, hydrates, co-crystals, or salts. Such APIs can also be prepared to have different physical forms. For example, the APIs may be amorphous, may have different crystalline polymorphs, or may exist in different solvation or hydration states. By varying the form of an API, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapour pressure, density, colour, and compressibility. Accordingly, variation of the crystalline state of an API is one of many ways in which to modulate the physical properties thereof.

It would be advantageous to have new forms of these APIs that have improved properties, in particular, as oral formulations. Specifically, it is desirable to identify improved forms of APIs that exhibit significantly improved properties including increased aqueous solubility and stability. Further, it is desirable to improve the processability, or preparation of pharmaceutical formulations. For example, needle-like crystal forms or habits of APIs can cause aggregation, even in compositions where the API is mixed with other substances, such that a non-uniform mixture is obtained. Needle-like morphologies can also give rise to filtration problems (See e.g., Mirmehrabi et al. J. Pharm. Sci. Vol. 93, No. 7, pp. 1692-1700, 2004). It is also desirable to increase the dissolution rate of API-containing pharmaceutical compositions in water, increase the bioavailability of orally-administered compositions, and provide a more rapid onset to therapeutic effect. It is also desirable to have a form of the API which, when administered to a subject, reaches a peak plasma level faster, has a longer lasting therapeutic plasma concentration, and higher overall exposure when compared to equivalent amounts of the API in its presently-known form.

Modafinil, an API used to treat subjects with narcolepsy, is practically insoluble in water. Modafinil (CAS Registry Number: 68693-11-8) is represented by the structure (I):

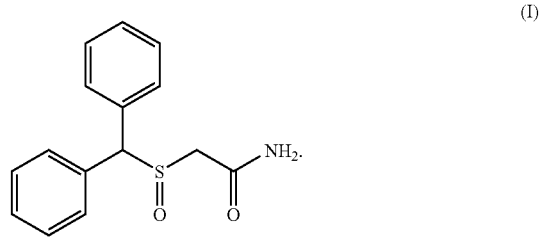

(I)

Modafinil is a chiral molecule due to the chiral S=O group. Therefore, modafinil exists as two isomers, R-(−)-modafinil and S-(+)-modafinil. It would be advantageous to have new forms of modafinil that have improved properties, in particular, as oral formulations. Specifically, it is desirable to identify improved forms of modafinil that exhibit significantly increased aqueous solubilities and both chemical and form stability. It is also desirable to increase the dissolution rate of API-containing pharmaceutical compositions in water, increase the bioavailability of orally-administered compositions, and provide a more rapid onset to therapeutic effect. It is also desirable to have a form of the API which, when administered to a subject, reaches a peak plasma level faster and/or has a longer lasting plasma concentration and higher overall exposure at high doses when compared to equivalent amounts of the API in its presently-known form.

SUMMARY OF THE INVENTION

It has now been found that polymorphs and solvates of modafinil can be obtained. Some of which can have different properties as compared to the free form of the API.

Embodiments of the present invention including, but not limited to, polymorphs and solvates can comprise racemic modafinil, enantiomerically pure modafinil (i.e., R-(−)-modafinil or S-(+)-modafinil), or enriched modafinil (e.g., between about 55 and about 90 percent ee). Similarly, solvent molecules (e.g., in a solvate) can also exist as racemic, enantiomerically pure, or an enriched form in embodiments of the present invention.

In another embodiment, the present invention provides the following modafinil solvates: chloroform, chlorobenzene, ethyl acetate, and acetic acid.

The processes according to the present invention may each comprise a further step or steps in which a modafinil polymorph or solvate produced thereby is incorporated into a pharmaceutical composition.

In a further embodiment, the present invention provides a novel polymorph of R-(−)-modafinil. In a specific embodiment, the present invention provides Forms III, IV, and V of R-(−)-modafinil. The present invention also provides a method of making a polymorph of R-(−)-modafinil.

In a further embodiment, the present invention provides a method of making a polymorph of R-(−)-modafinil, comprising:
  (a) providing R-(−)-modafinil;
  (b) crystallizing the polymorph of R-(−)-modafinil from an appropriate solvent.

In a further embodiment, a polymorph of R-(−)-modafinil is crystallized from an organic solvent. In particular embodiments, the organic solvent can be acetonitrile, dimethyl formamide (DMF), methanol, methyl ethyl ketone, N-methylpyrrolidone, ethanol, isopropanol, isobutanol, formamide, isobutyl acetate, 1,4-dioxane, tetrahydrofuran (THF), ethyl acetate, o-xylene, isopropyl acetate, dichloromethane, propylene glycol, acetic acid, water, acetone, nitromethane, toluene, and benzyl alcohol. Both pure solvents and mixed solvents are considered organic solvent, according to the present invention. In a particular embodiment, the organic solvent is ethanol. In another embodiment, a mixed solvent system is used to crystallize a polymorph of R-(−)-modafinil. Mixed solvent systems can be, for example, ethanol and isopropyl alcohol, or ethyl acetate and ethanol. In a further embodiment, the crystallization in step (b) is completed via thermal crystallization. In a further embodiment, the crystallization in step (b) is completed via evaporation of the solvent.

In another embodiment, a pharmaceutical composition comprises a modified release profile of one or more of racemic modafinil, R-(−)-modafinil, and S-(+)-modafinil. The modified release profile can comprise, for example, two or more maxima of plasma concentration, such as a dual-release profile.

The invention further provides a medicament comprising a polymorph or a solvate of modafinil and methods of making the same. Typically, the medicament further comprises one or more pharmaceutically-acceptable carriers, diluents or excipients. Medicaments according to the invention are described in further detail below.

The processes according to the present invention may each comprise a further step or steps in which the modafinil polymorph or solvate produced thereby is incorporated into a medicament.

In a still further aspect of the invention, a method is provided for treating a subject, preferably a human subject, suffering from excessive daytime sleepiness associated with narcolepsy, multiple sclerosis related fatigue, infertility, eating disorders, attention deficit hyperactivity disorder (ADHD), Parkinson's disease, incontinence, sleep apnea, or myopathies where modafinil is an effective active pharmaceutical for said disorder. The method comprises administering to the subject a therapeutically-effective amount of a polymorph or a solvate of modafinil.

In another embodiment, a method is provided for treating a subject suffering from one or more of the above mentioned conditions or disorders, including, but not limited to sleep disorders such as narcolepsy, comprising administering to the subject a therapeutically-effective amount of R-(−)-modafinil Form III, R-(−)-modafinil Form IV, or R-(−)-modafinil Form V.

DETAILED DESCRIPTION OF THE INVENTION

Figure 1:
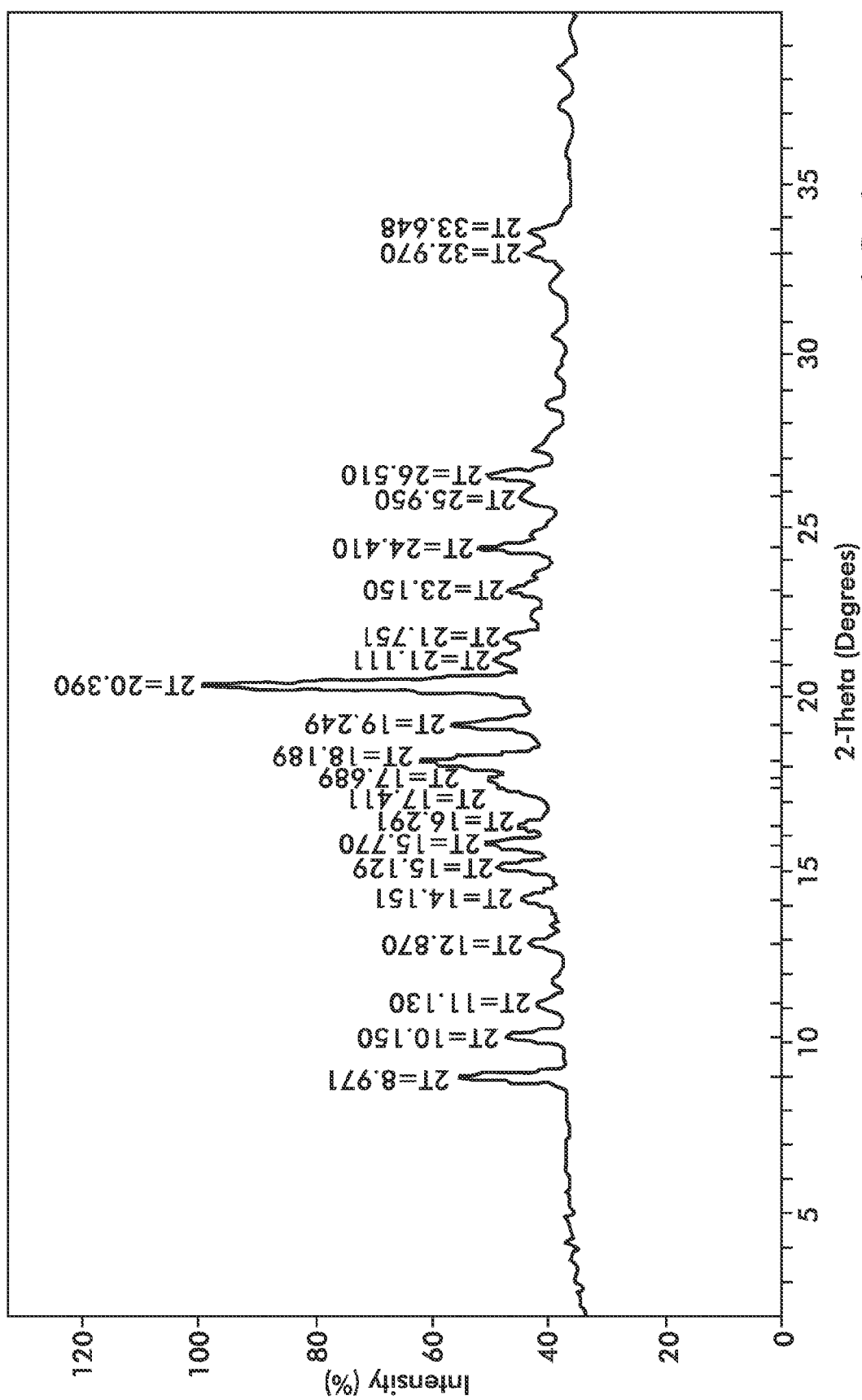
FIG. 1—PXRD diffractogram of polymorph of 2:1 R-(−)-modafinil:S-(+)-modafinil.

The structure of modafinil includes a stereocenter and, therefore, can exist as a racemate, one of two pure isomers, or any ratio of the two isomeric pairs. The chemical name of racemic modafinil is (±)-2-[(Diphenylmethyl) sulfinyl]acetamide. The isomeric pairs of racemic modafinil are R-(−)-2-[(Diphenylmethyl) sulfinyl]acetamide or R-(−)-modafinil and S-(+)-2-[(Diphenylmethyl) sulfinyl]acetamide or S-(+)-modafinil.

As used herein and unless otherwise specified, the term "enantiomerically pure" includes a composition which is substantially enantiomerically pure and includes, for example, a composition with greater than or equal to about 90, 91, 92, 93, 94, 95, 96, 97, 98, or 99 percent enantiomeric excess. Enantiomeric excess is defined by percent enantiomer A−percent enantiomer B, or by the formula:

ee percent=100*([*R*]−[*S*]/([*R*]+[*S*]), where *R* is moles of R-(−)-modafinil and *S* is moles of S-(+)-modafinil.

As used herein, the term "modafinil" includes the racemate, other mixtures of R- and S-isomers, and single enantiomers, but may be specifically set forth as the racemate, R-isomer, S-isomer, or any mixture of both R- and S-isomers.

As used herein and unless otherwise specified, the term "racemic" refers to a material (e.g., a polymorph or a solvate) which is comprised of an equimolar mixture of the enantiomers of modafinil, the solvent, or both. For example, a solvate comprising modafinil and a non-stereoisomeric solvent molecule is a "racemic solvate" only when there is present an equimolar mixture of the modafinil enantiomers. Similarly, a solvate comprising modafinil and a stereoisomeric solvent molecule is a "racemic solvate" only when there is present an equimolar mixture of the modafinil enantiomers and of the solvent molecule enantiomers.

As used herein and unless otherwise specified, the term "enantiomerically pure" refers to a material which is comprised of modafinil, and optionally, a stereoisomeric or non-stereoisomeric solvent molecule, where the enantiomeric excess of the stereoisomeric species is greater than or equal to about 90 percent ee (enantiomeric excess).

For purposes of the present invention, the chemical and physical properties of modafinil in the form of a solvate or a polymorph may be compared to a reference compound that is modafinil in a different form. The reference compound may be specified as a free form, or more specifically, an anhydrate or hydrate of a free form, or more specifically, for example, a hemihydrate, monohydrate, dihydrate, trihydrate, quadrahydrate, pentahydrate; or a solvate of a free form. The reference compound may also be specified as crystalline or amorphous. The reference compound may also be specified as the most stable polymorph known of the specified form of the reference compound.

Modafinil and some solvent molecules of the present invention have one or more chiral centers and may exist in a variety of stereoisomeric configurations. As a consequence of these chiral centers, modafinil and several solvates of the present invention occur as racemates, mixtures of enantiomers and as individual enantiomers, as well as diastereomers and mixtures of diastereomers. All such racemates, enantiomers, and diastereomers are within the scope of the present invention including, for example, cis- and trans-isomers, R- and S-enantiomers, and (D)- and (L)-isomers. Solvates of the present invention can include isomeric forms of either modafinil or the solvent molecules or both. Isomeric forms of modafinil and solvent molecules include, but are not limited to, stereoisomers such as enantiomers and diastereomers. In one embodiment, a solvate comprises racemic modafinil and a solvent molecule. In another embodiment, a solvate comprises enantiomerically pure R- or S-modafinil and a solvent molecule. In another embodiment, a solvate of the present invention comprises modafinil and/or a solvent molecule with an enantiomeric excess of about 1 percent, 2 percent, 3 percent, 4 percent, 5 percent, 10 percent, 15 percent, 20 percent, 25 percent, 30 percent, 35 percent, 40 percent, 45 percent, 50 percent, 55 percent, 60 percent, 65 percent, 70 percent, 75 percent, 80 percent, 85 percent, 90 percent, 95 percent, 96 percent, 97 percent, 98 percent, 99 percent, greater than 99 percent, or any intermediate value. In another embodiment, a polymorph or a solvate of the present invention can comprise modafinil with an enantiomeric excess of about 1 percent, 2 percent, 3 percent, 4 percent, 5 percent, 10 percent, 15 percent, 20 percent, 25 percent, 30 percent, 35 percent, 40 percent, 45 percent, 50 percent, 55 percent, 60 percent, 65 percent, 70 percent, 75 percent, 80 percent, 85 percent, 90 percent, 95 percent, 96 percent, 97 percent, 98 percent, 99 percent, greater than 99 percent, or any intermediate value.

"Enriched" modafinil, according to the present invention, comprises both the R-(−)- and S-(+)-isomers of modafinil in amounts greater than or equal to about 5, 6, 7, 8, 9, or 10 percent by weight and less than or equal to about 90, 91, 92, 93, 94, or 95 percent by weight. For example, a composition comprising 67 percent by weight R-(−)-modafinil and 33 percent by weight S-(+)-modafinil is an enriched modafinil composition. In such an example, the composition is neither racemic nor enantiomerically pure. The term "enriched R-(−)-modafinil" may be used to describe a composition of modafinil with greater than 50 percent R-(−)-modafinil and less than 50 percent S-(+)-modafinil. Likewise, the term "enriched S-(+)-modafinil" may be used to describe a composition of modafinil with greater than 50 percent S-(+)-modafinil and less than 50 percent R-(−)-modafinil.

The terms "R-(−)-modafinil" and "S-(+)-modafinil" can be used to describe enriched modafinil, enantiomerically pure modafinil, or substantially enantiomerically pure modafinil, but may also specifically exclude enriched modafinil, enantiomerically pure modafinil, and/or substantially enantiomerically pure modafinil.

Solvates and polymorphs comprising enantiomerically pure and/or enantiomerically enriched components (e.g., modafinil or solvent molecule) can give rise to chemical and/or physical properties which are modulated with respect to those of the corresponding form comprising a racemic component.

Polymorphs and solvates of modafinil can be prepared with racemic modafinil, enantiomerically pure modafinil, or with any mixture of R-(−)- and S-(+)-modafinil (e.g., enriched modafinil) according to the present invention.

In another embodiment, the compositions or medicaments including solvates and polymorphs of the present invention can be compared with free form modafinil as found in PROVIGIL® (Cephalon, Inc.). (See U.S. Reissued Pat. No. RE37,516)

In another embodiment, the present invention provides the following modafinil solvates: chloroform, chlorobenzene, ethyl acetate, and acetic acid.

Pharmaceutically acceptable forms can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Chemg-ju, Controlled Release Dosage Form Design, 2 Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the solvates, polymorphs and compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed polymorphs and thus effect controlled delivery of the drug. Examples of specific anion exchangers include, but are not limited to, Duolite® A568 and Duolite® AP143 (Rohm & Haas, Spring House, Pa. USA).

One embodiment of the invention encompasses a unit dosage form which comprises a pharmaceutically acceptable solvate, hydrate, dehydrate, anhydrous, or amorphous form thereof, and one or more pharmaceutically acceptable excipients or diluents, wherein the pharmaceutical composition, medicament or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder into a hard tablet, coating the tablet with cellulose derivatives to form a semi-permeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively deliver drugs with low water solubility. Id. at 234.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a polymorph, or a solvate, hydrate, dehydrate, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a polymorph, or a solvate, hydrate, dehydrate, anhydrous, or amorphous form thereof. See U.S. Pat. No. 6,342,249, the entirety of which is incorporated herein by reference.

In another embodiment, a pharmaceutical composition or medicament comprises a mixture of a novel form of modafinil of the present invention (e.g., a polymorph or solvate) and racemic modafinil. This embodiment can be used, for example, as a controlled-, sustained-, or extended-release dosage form. In another embodiment, an extended-release dosage form comprises racemic modafinil and a polymorph or a solvate of the present invention.

In another embodiment, a pharmaceutical composition or medicament comprises a modified release profile of one or more of racemic modafinil, R-(−)-modafinil, and S-(+)-modafinil. The modified release profile can comprise, for example, two or more maxima of plasma concentration, such as a dual-release profile. Such a modified release profile may aid a patient treated with a composition or medicament of the present invention who experiences loss of wakefulness in the afternoon, for example. A second "burst" or release of API at least 2, 3, 4, 5, or 6 hours after administration may help to overcome such an effect. In another embodiment, a pharmaceutical composition or medicament comprising a small loading dose released immediately following administration can be employed, followed by an approximate zero-order release profile over the following 2, 3, 4, 5, or 6 hours. In such a composition, peak plasma levels can be reached at about midday.

In another embodiment, a pharmaceutical composition or medicament comprising a modified release profile of modafinil can comprise R-(−)-modafinil and S-(+)-modafinil wherein the R-(−)-modafinil provides an initial increase (initial $C_{max}$ due to R-(−)-modafinil) in plasma concentration and the S-(+)-modafinil provides a delayed increase (subsequent $C_{max}$ due to S-(+)-modafinil) in plasma concentration. The delayed increase in $C_{max}$ due to S-(+)-modafinil can be 2, 3, 4, 5, 6 hours or more after the initial $C_{max}$ due to R-(−)-modafinil. In another embodiment, the delayed $C_{max}$ is approximately equal to the initial $C_{max}$. In another embodiment, the delayed $C_{max}$ is greater than the initial $C_{max}$. In another embodiment, the delayed $C_{max}$ is less than the initial $C_{max}$. In another embodiment, the delayed $C_{max}$ is due to racemic modafinil, instead of S-(+)-modafinil. In another embodiment, the delayed $C_{max}$ is due to R-(−)-modafinil, instead of S-(+)-modafinil. In another embodiment, the initial $C_{max}$ is due to racemic modafinil, instead of R-(−)-modafinil. In another embodiment, the initial $C_{max}$ is due to S-(+)-modafinil, instead of R-(−)-modafinil. In another embodiment, the modified release profile has 3, 4, 5, or more "bursts" in plasma concentration.

In another embodiment, a pharmaceutical composition or medicament comprising a modified release profile of modafinil wherein one or more of racemic modafinil, R-(−)-modafinil, or S-(+)-modafinil are present in the form of a solvate or a polymorph.

In another embodiment, a pharmaceutical composition or medicament comprising a modified release profile wherein R-(−)-modafinil is used in an oral formulation. Such a composition can minimize first-pass metabolism of modafinil to the sulfone. In another embodiment, a pharmaceutical composition or medicament comprising a modified release profile wherein racemic modafinil is used in an oral formulation. In another embodiment, a pharmaceutical composition or medicament comprising a modified release profile wherein S-(+)-modafinil is used in an oral formulation. In another embodiment, a pharmaceutical composition or medicament comprising a modified release profile wherein racemic modafinil and R-(−)-modafinil are used in an oral formulation. In another embodiment, a pharmaceutical composition or medicament comprising a modified release profile wherein racemic modafinil and S-(+)-modafinil are used in an oral formulation. In another embodiment, a pharmaceutical composition or medicament comprising a modified release profile wherein S-(+)-modafinil and R-(−)-modafinil are used in an oral formulation. In another embodiment, a pharmaceutical composition or medicament comprising a modified release profile wherein racemic modafinil, S-(+)-modafinil and R-(−)-modafinil are used in an oral formulation.

In another embodiment, a pharmaceutical composition or medicament comprising a modified release profile of modafinil is administered transdermally. Such a transdermal (TD) delivery can avoid first-pass metabolism. Additionally, a "pill-and-patch" strategy can be taken, where only a fraction of the daily dose is delivered through the skin to generate basal systemic levels, onto which oral therapy is added to ensure the wakefulness effect.

Excipients employed in pharmaceutical compositions and medicaments of the present invention can be solids, semi-solids, liquids or combinations thereof. Preferably, excipients are solids. Compositions and medicaments of the invention containing excipients can be prepared by known technique of pharmacy that comprises admixing an excipient with an API or therapeutic agent. A pharmaceutical composition or medicament of the invention contains a desired amount of API per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the API, such as tablets or capsules.

Non-limiting examples follow of excipients that can be used to prepare pharmaceutical compositions or medicaments of the invention.

Pharmaceutical compositions and medicaments of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with APIs. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of APIs, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions and medicaments of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colocorn™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions and medicaments of the present invention.

Pharmaceutical compositions and medicaments of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of an API of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition or medicament.

Many of the binding agents are polymers comprising amide, ester, ether, alcohol or ketone groups and, as such, are preferably included in pharmaceutical compositions and medicaments of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions and medicaments of the invention optionally comprise one or more pharmaceutically acceptable wetting agents as excipients. Such wetting agents are preferably selected to maintain the API in close association with water, a condition that is believed to improve bioavailability of the composition.

Non-limiting examples of surfactants that can be used as wetting agents in pharmaceutical compositions and medicaments of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition or medicament.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition or medicament.

Pharmaceutical compositions and medicaments of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition or medicament.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition or medicament.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions and medicaments of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions and medicaments of the invention. When present in pharmaceutical compositions and medicaments of the invention to promote dosage form disintegration, one or more effervescent agents are preferably present in a total amount of about 30% to about 75%, and preferably about 45% to about 70%, for example about 60%, by weight of the pharmaceutical composition or medicament.

According to a particularly preferred embodiment of the invention, an effervescent agent, present in a solid dosage form in an amount less than that effective to promote disintegration of the dosage form, provides improved dispersion of the API in an aqueous medium. Without being bound by theory, it is believed that the effervescent agent is effective to accelerate dispersion of the API, from the dosage form in the gastrointestinal tract, thereby further enhancing absorption and rapid onset of therapeutic effect. When present in a pharmaceutical composition or medicament of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the pharmaceutical composition or medicament.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid acids useful in the invention include citric acid, tartaric acid (as D-, L-, or D/L-tartaric acid), malic acid, maleic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize metal salts of APIs typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions and medicaments are advantageously administered orally.

Pharmaceutical compositions and medicaments of the present invention can comprise about 10% to about 50%, about 25% to about 50%, about 30% to about 45%, or about 30% to about 35% by weight of API; about 10% to about 50%, about 25% to about 50%, about 30% to about 45%, or about 30% to about 35% by weight of a an excipient which inhibits crystallization; and about 5% to about 50%, about 10% to about 40%, about 15% to about 35%, or about 30% to about 35% by weight of a binding agent. In one example, the weight ratio of the API to the excipient which inhibits crystallization to binding agent is about 1 to 1 to 1.

Solid dosage forms of the invention can be prepared by any suitable process, not limited to processes described herein.

An illustrative process comprises (a) a step of blending a salt of the invention with one or more excipients to form a blend, and (b) a step of tableting or encapsulating the blend to form tablets or capsules, respectively.

In a preferred process, solid dosage forms are prepared by a process comprising (a) a step of blending an API salt of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in API content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein the API is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

In another embodiment of the present invention, a pharmaceutical composition or medicament comprising modafinil and an additional API can be prepared. The modafinil and the additional API can be included as a mixture or a combination of active pharmaceutical ingredients. For example, a composition can comprise modafinil and caffeine as a combination. A composition comprising modafinil and caffeine can be used as a therapeutic agent to treat the same conditions as modafinil. In such a composition comprising modafinil and caffeine, the caffeine can yield a quick release characteristic (small $T_{max}$ relative to modafinil) to the dissolution profile while the modafinil causes the therapeutic effect to be present for hours after administration. For example, the $T_{max}$ of caffeine may be 0.001, 0.01, 0.05, 0.1, 0.2, 0.3, 0.4, 0.5, 0.6, 0.7, or 0.8 times that of modafinil. Combination therapies comprise the administration of two or more APIs in the same formulation, or in two or more co-administered formulations. The APIs can be administered together at the same time, or individually at specified intervals.

In a further embodiment, the present invention provides a novel polymorph of R-(−)-modafinil. In a specific embodiment, the present invention provides Forms III, IV, and V of R-(−)-modafinil. The present invention also provides a method of making a polymorph of R-(−)-modafinil.

In a further embodiment, the present invention provides a method of making a polymorph of R-(−)-modafinil, comprising:

(a) providing R-(−)-modafinil; and
(b) crystallizing the polymorph of R-(−)-modafinil from an appropriate solvent.

In a further embodiment, a polymorph of R-(−)-modafinil is crystallized from an organic solvent. In a particular embodiment, the organic solvent is ethanol. In another embodiment, a mixed solvent system is used to crystallize a polymorph of R-(−)-modafinil. Mixed solvent systems can be, for example, ethanol and isopropyl alcohol, or ethyl acetate and ethanol. In a further embodiment, the crystallization in step (b) is completed via thermal recrystallization. In a further embodiment, the crystallization in step (b) is completed via evaporation of the solvent.

Uses for modafinil are well known in the art and include the treatment of narcolepsy, multiple sclerosis related fatigue, infertility, eating disorders, attention deficit hyperactivity disorder (ADHD), Parkinson's disease, incontinence, sleep apnea, or myopathies. In another embodiment, any one or more of the modafinil compositions of the present invention may be used in the treatment of one or more of the above conditions. The dosage and administration for modafinil compositions of the present invention can be determined using routine methods in the art but will generally fall between about 50 and about 700 mg/day.

In another embodiment, a method is provided for treating a subject suffering from one or more of the above mentioned conditions or disorders, including, but not limited to sleep disorders such as narcolepsy, comprising administering to the subject a therapeutically-effective amount of R-(−)-modafinil Form III, R-(−)-modafinil Form IV, or R-(−)-modafinil Form V.

In another embodiment, a composition of the present invention can be administered to a mammal via an injection. Injections include, but are not limited to, intravenous, subcutaneous, and intramuscular injections. In another embodiment, a composition of the present invention is formulated for injection into a mammal in need of therapeutic effect.

EXAMPLES

Analytical Methods

Differential scanning calorimetric (DSC) analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/98/2000/NT, version 3.1E; Build 3.1.0.40 (2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing the modafinil sample in an aluminum pan with a crimped pan closure. The starting temperature was typically 20 degrees C. with a heating rate of 10 degrees C./minute, and the ending temperature was 200 degrees C. All reported DSC transitions represent the temperature of endothermic or exothermic transition at their respective peaks with an error of +/−2 degrees C., unless otherwise indicated.

Thermogravimetric analysis (TGA) of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/98/2000/NT, version 3.1E; Build 3.1.0.40 (2001 TA Instruments-Water LLC).

For the TGA experiments, the purge gas used was dry nitrogen, the balance purge was 40 mL/minute $N_2$, and the sample purge was 60 mL/minute $N_2$.

TGA was performed on the sample by placing the modafinil sample in a platinum pan. The starting temperature was typically 20 degrees C. with a heating rate of 10 degrees C./minute, and the ending temperature was 300 degrees C.

A powder X-ray diffraction (PXRD) pattern for the samples was obtained using a D/Max Rapid, Contact (Rigaku/MSC, The Woodlands, Tex., U.S.A.), which uses as its control software RINT Rapid Control Software, Rigaku Rapid/XRD, version 1.0.0 (1999 Rigaku Co.). In addition, the analysis software used were RINT Rapid display software, version 1.18 (Rigaku/MSC), and JADE XRD Pattern Processing, versions 5.0 and 6.0 ((1995-2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-60 degrees; the integration chi range was 0-360 degrees; the number of chi segments was 1; the step size used was 0.02; the integration utility was cylint; normalization was used; dark counts were 8; omega offset was 180; and chi and phi offsets were 0.

PXRD diffractograms were also acquired via the Bruker AXS D8 Discover X-ray Diffractometer. This instrument was equipped with GADDS™ (General Area Diffraction Detection System), a Bruker AXS HI-STAR Area Detector at a distance of 15.05 cm as per system calibration, a copper source (Cu/$K_\alpha$ 1.54056 angstroms), automated x-y-z stage, and 0.5 mm collimator. The sample was compacted into pellet form and mounted on the x-y-z stage. A diffractogram was acquired under ambient conditions (25 degrees C.) at a powder setting of 40 kV and 40 mA in reflection mode while the sample remained stationary. The exposure time was varied and specified for each sample. The diffractogram obtained underwent a spatial remapping procedure to account for the geometrical pincushion distortion of the area detector then integrated along chi from −118.8 to −61.8 degrees and 2-theta 2.1-37 degrees at a step size of 0.02 degrees with normalization set to bin normalize.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.1 degrees 2-theta.

For PXRD data herein, including Tables and Figures, each composition of the present invention may be characterized by any one, any two, any three, any four, any five, any six, any seven, or any eight or more of the 2 theta angle peaks. Any one, two, three, four, five, or six DSC transitions can also be used to characterize the compositions of the present invention. The different combinations of the PXRD peaks and the DSC transitions can also be used to characterize the compositions.

Thermal (hotstage) microscopy was completed on a Zeiss Axioplan 2 microscope equipped with a Mettler Toledo FP90 controller. The hotstage used was a Mettler Toledo FP82HT. All melting point determinations were completed by placing the sample on a microscope slide and covered with a coverslip. The initial temperature was set at 30 degrees C. and the temperature was increased at a rate of 10 degrees C./minute. Melting was observed through a 5× microscope objective.

HPLC Method: (adapted from Donovan et al. Therapeutic Drug Monitoring 25:197-202.
Column: Astec Cyclobond 12000 RSP 250×4.6 mm (Part No. 411121)
Mobile Phase A: 20 mM sodium phosphate, pH 3.0
 B: 70:30 mobile phase A:acetonitrile
 Flow Rate: 1.0 mL/min (1500 PSI)
 Flow Program: gradient
Run Time: 35 minutes
Detection: UV@ 225 nm
Injection Volume: 10 microliters
Column Temperature: 30+/−1 degrees C.
Standard diluent: 90:10 (v/v) Mobile Phase A:acetonitrile
Needle wash: acetonitrile
Purge solvent & seal wash: 90:10 (v/v) water:acetonitrile
Mobile Phase Preparation:
1. Prep 1 M sodium phosphate monobasic: dissolve 120 g of sodium phosphate monobasic in water and make up to 1000 mL; filter.
2. Prep Mobile Phase A (20 mM sodium phosphate, pH 3.0): for each liter, dilute 20 mL 1 M sodium phosphate to 1000 mL with water; adjust pH to 3.0 with phosphoric acid.
3. Prep Mobile Phase B (70:30 (v/v) 20 mM sodium phosphate, pH 3.0:acetonitrile): for each liter, mix 700 mL Mobile Phase A and 300 mL of acetonitrile.
Sample Prep:
1. Dissolve samples in 90:10 (v/v) 20 mM sodium phosphate, pH 3.0:acetonitrile to an approximate concentration of 20 micrograms/mL Raman Acquisitions The sample was either left in the glass vial in which it was processed or an aliquot of the sample was transferred to a glass slide. The glass vial or slide was positioned in the sample chamber. The measurement was made using an Almega™ Dispersive Raman (Almega™ Dispersive Raman, Thermo-Nicolet, 5225 Verona Road, Madison, Wis. 53711-4495) system fitted with a 785 nm laser source. The sample was manually brought into focus using the microscope portion of the apparatus with a 10× power objective (unless otherwise noted), thus directing the laser onto the surface of the sample. The spectrum was acquired using the parameters outlined in Table A. (Exposure times and number of exposures may vary; changes to parameters will be indicated for each acquisition.)

TABLE A

Raman Spectral acquisition parameters

| Parameter | Setting Used |
| --- | --- |
| Exposure time (s) | 2.0 |
| Number of exposures | 10 |
| Laser source wavelength (nm) | 785 |
| Laser power (%) | 100 |
| Aperture shape | pin hole |
| Aperture size (um) | 100 |
| Spectral range | 104-3428 |
| Grating position | Single |
| Temperature at acquisition (degrees C.) | 24.0 |

IR Acquisitions

IR spectra were obtained using Nexus™ 470 FT-IR, Thermo-Nicolet, 5225 Verona Road, Madison, Wis. 53711-4495 and were analyzed with Control and Analysis software: OMNIC, Version 6.0a, (C) Thermo-Nicolet, 1995-2004.

Example 1

2:1 R-(−)-modafinil:S-(+)-modafinil

Anhydrous ammonia gas was bubbled through a solution containing R-benzhydrylsulfinyl methyl ester (8.62 g, 0.0299 mol, about 80:20 R-isomer:S-isomer by weight) in methanol (125 mL) for 10 minutes. The pressure build-up from the reaction caused a back flow of sodium bicarbonate from the trap into the reaction mixture. The reaction was stopped and the precipitate was collected. The filtrate was concentrated under reduced pressure to give a yellow solid residue (2.8 g). The yellow solid was passed through a column (silica gel, grade 9385, 230-400, mesh 60 angstroms), 3:1 v/v ethyl acetate:hexane as eluent). The filtrates were then combined and concentrated under reduced pressure to give a slightly yellow solid (most of the yellow color remained on the column). The solid was then re-crystallized from ethanol by heating the mixture until it was boiling and then cooling to room temperature to give 2:1 R-(−)-modafinil:S-(+)-modafinil as a colorless solid (580 mg). PXRD and DSC analysis were completed on the obtained solid and it was determined that the solid is a pure form of R-(−)-modafinil and S-(+)-modafinil in an approximate 2:1 ratio by weight.

The 2:1 R-(−)-modafinil:S-(+)-modafinil solid obtained above can be characterized by any one, any two, any three, any four, any five, or any six or more of the peaks in FIG. 1 including, but not limited to, 8.97, 10.15, 12.87, 14.15, 15.13, 15.77, 18.19, and 20.39 degrees 2-theta (data as collected).

Figure 2:
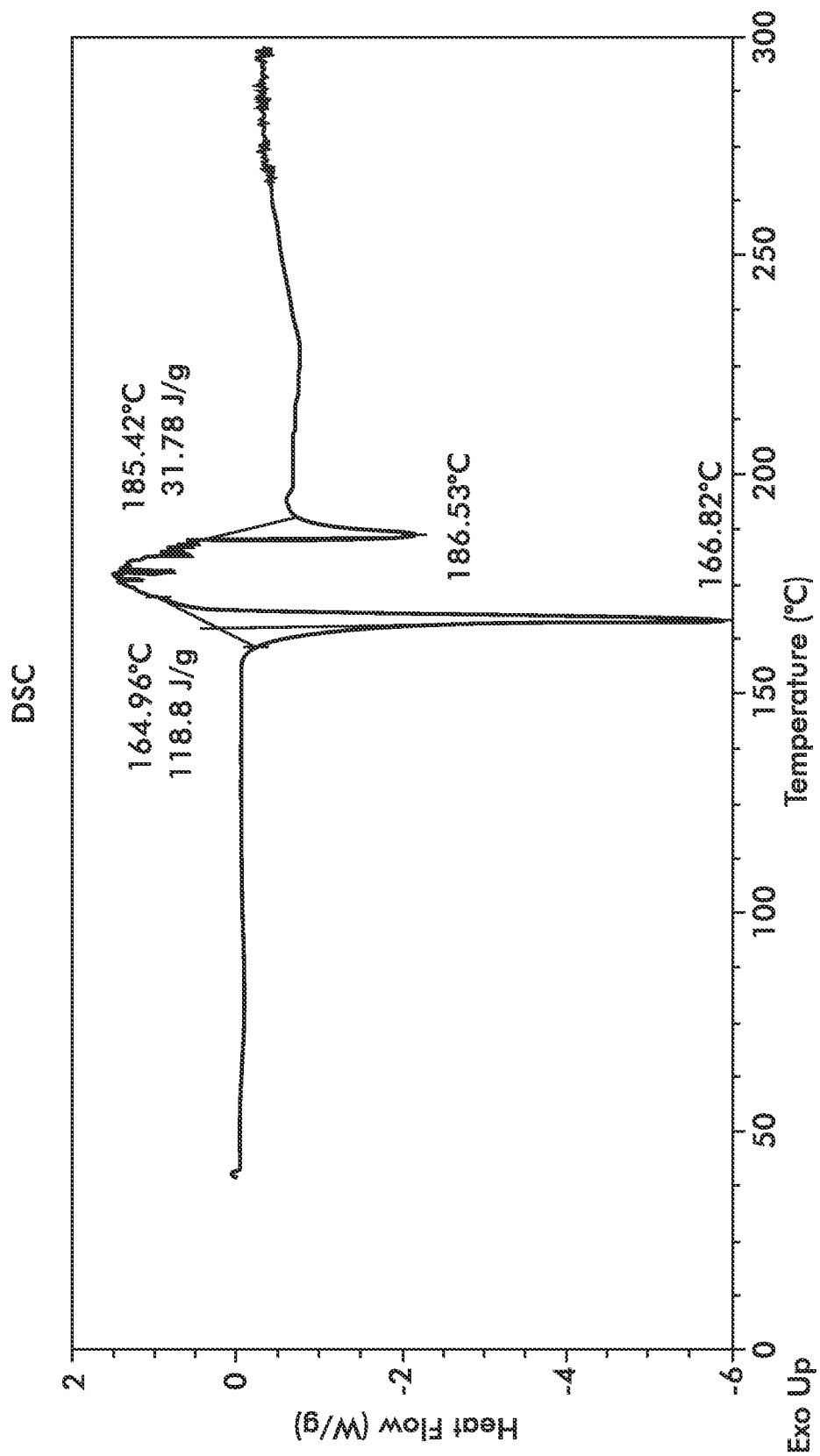
FIG. 2—DSC thermogram of polymorph of 2:1 R-(−)-modafinil:S-(+)-modafinil.

DSC of the solid described above showed an endothermic transition at about 167 degrees C. (See FIG. 2).

Example 2

Polymorphs of R-(−)-modafinil

Figure 3:
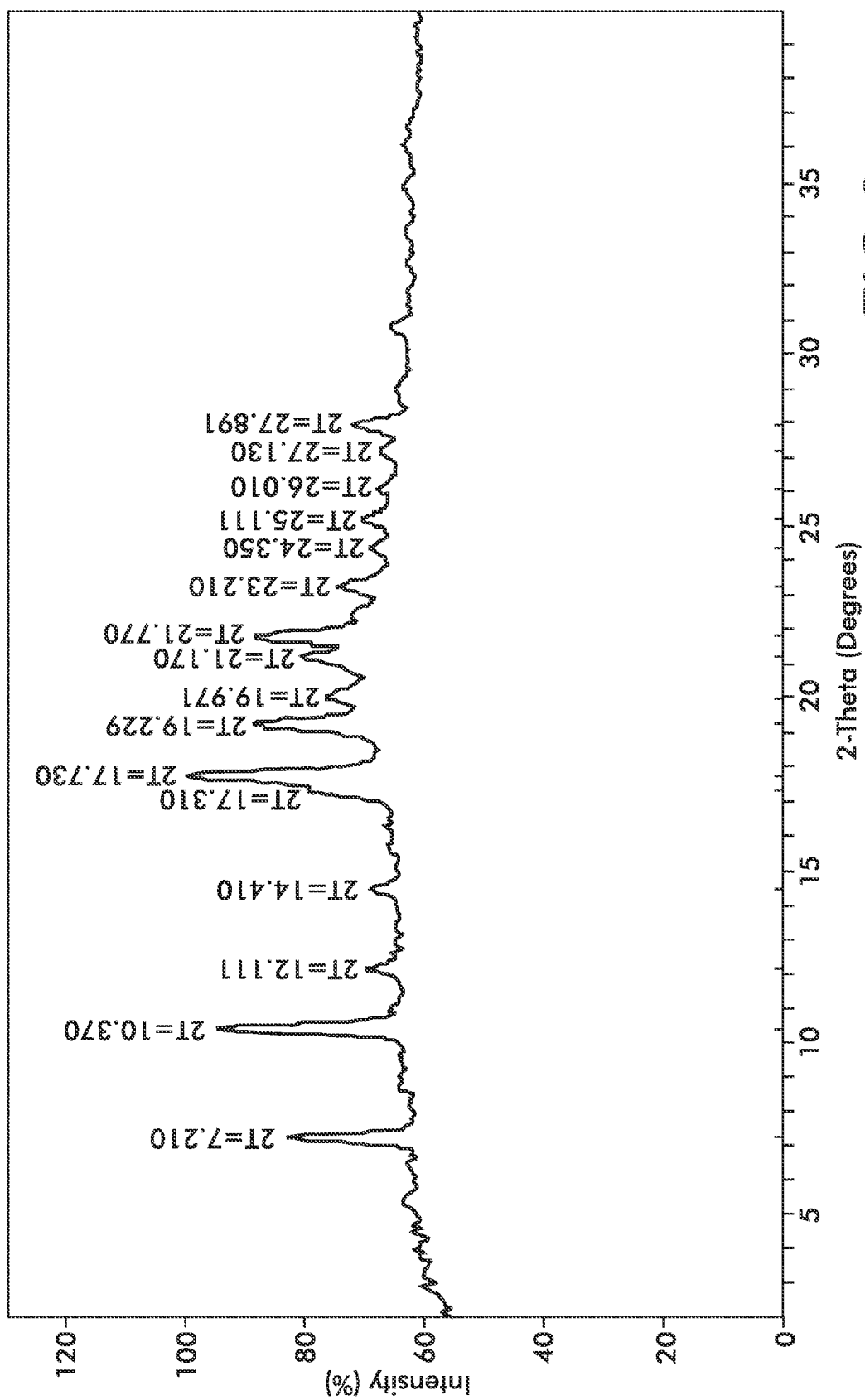
FIG. 3—PXRD diffractogram of a polymorph of R-(−)-modafinil (Form III).
Figure 6:
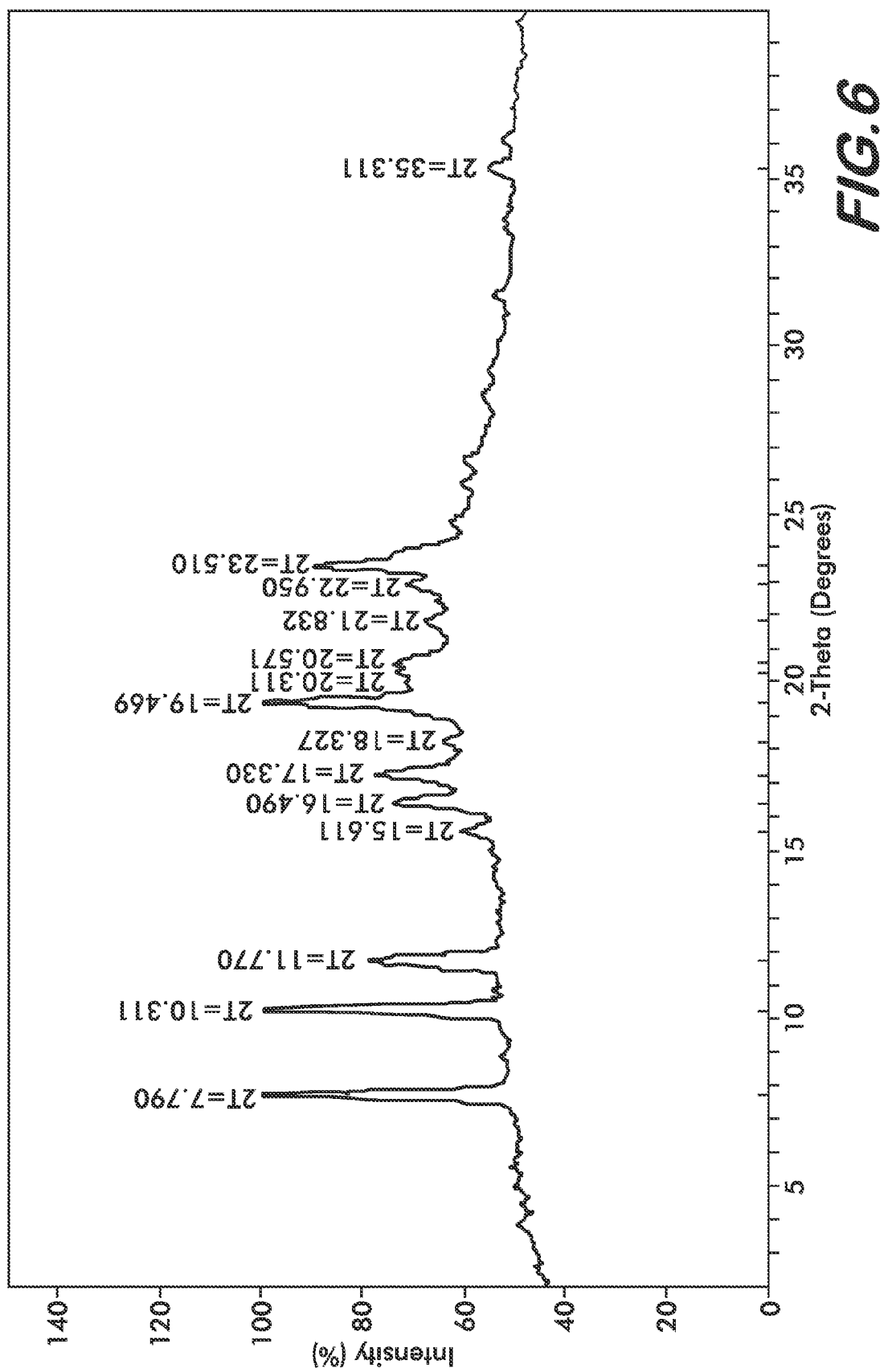
FIG. 6—PXRD diffractogram of a polymorph of R-(−)-modafinil (Form IV).
Figure 9:
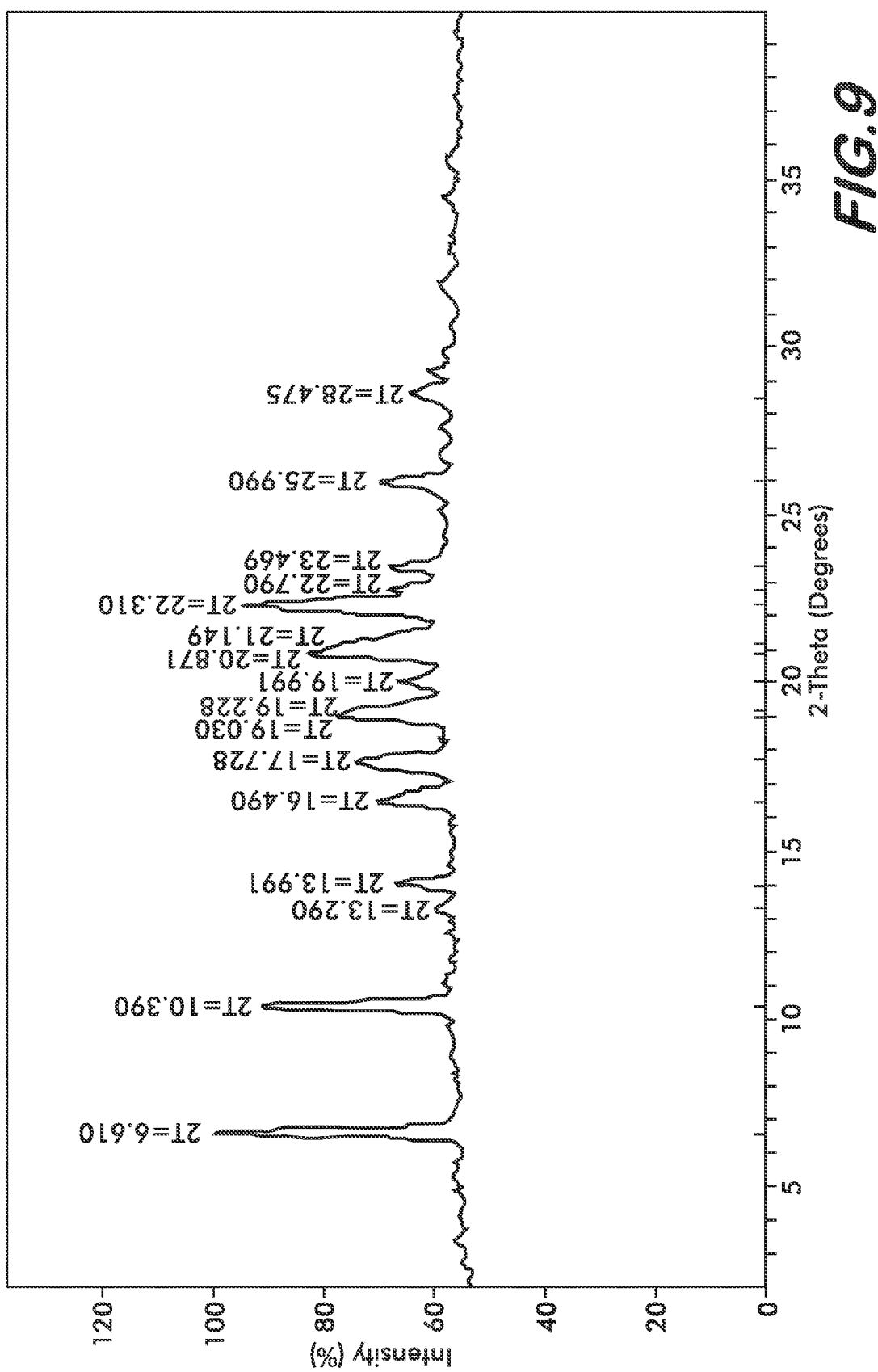
FIG. 9—PXRD diffractogram of a polymorph of R-(−)-modafinil (Form V).

Several polymorphs of R-(−)-modafinil have been observed, each characterized by PXRD. FIGS. 3, 6, and 9 show these PXRD diffractograms (data as collected) of polymorphs Form III, Form IV, and Form V.

Recrystallization has proved to be an effective technique for the formation and acquisition of the polymorphs of R-(−)-modafinil. Suitable solvents for the crystallization of one or more polymorphs of R-(−)-modafinil include, but are not limited to, acetonitrile, dimethyl formamide (DMF), methanol, methyl ethyl ketone, N-methylpyrollidone, ethanol, isopropanol, isobutanol, formamide, isobutyl acetate, 1,4-dioxane, tetrahydrofuran (THF), ethyl acetate, o-xylene, isopropyl acetate, dichloromethane, propylene glycol, acetic acid, water, acetone, nitromethane, toluene, and benzyl alcohol. Pure solvents and mixtures of solvents may be used to crystallize one or more polymorphs of R-(−)-modafinil.

R-(−)-modafinil Form III

Anhydrous ammonia gas was bubbled through a solution containing R-benzhydrylsulfinyl methyl ester (8.3 g, 0.0288 mol) in methanol (75 mL) for 10 minutes. The reaction was then stirred in a 5 degrees C. ice bath for 1 hour and ammonia gas was bubbled through for an additional 10 minutes. Stirring was continued for an additional 2 hours and ammonia was bubbled through again for 10 minutes. After stirring for another hour a precipitate had formed (575 mg) and was collected. The filtrate was then neutralized using conc. HCl and another precipitate formed and was collected. The solid residue was then re-crystallized from a 1:1 v/v mixture of ethanol and isopropyl alcohol by heating the mixture until it was boiling and then cooling to room temperature to give R-(−)-modafinil form III as a colorless solid (1.01 g).

R-(−)-modafinil Form III can be characterized by any one, any two, any three, any four, any five, or any six or more of the peaks in FIG. 3 including, but not limited to, 7.21, 10.37, 17.73, 19.23, 21.17, 21.77 and 23.21 degrees 2-theta (Rigaku PXRD, data as collected).

Figure 4:
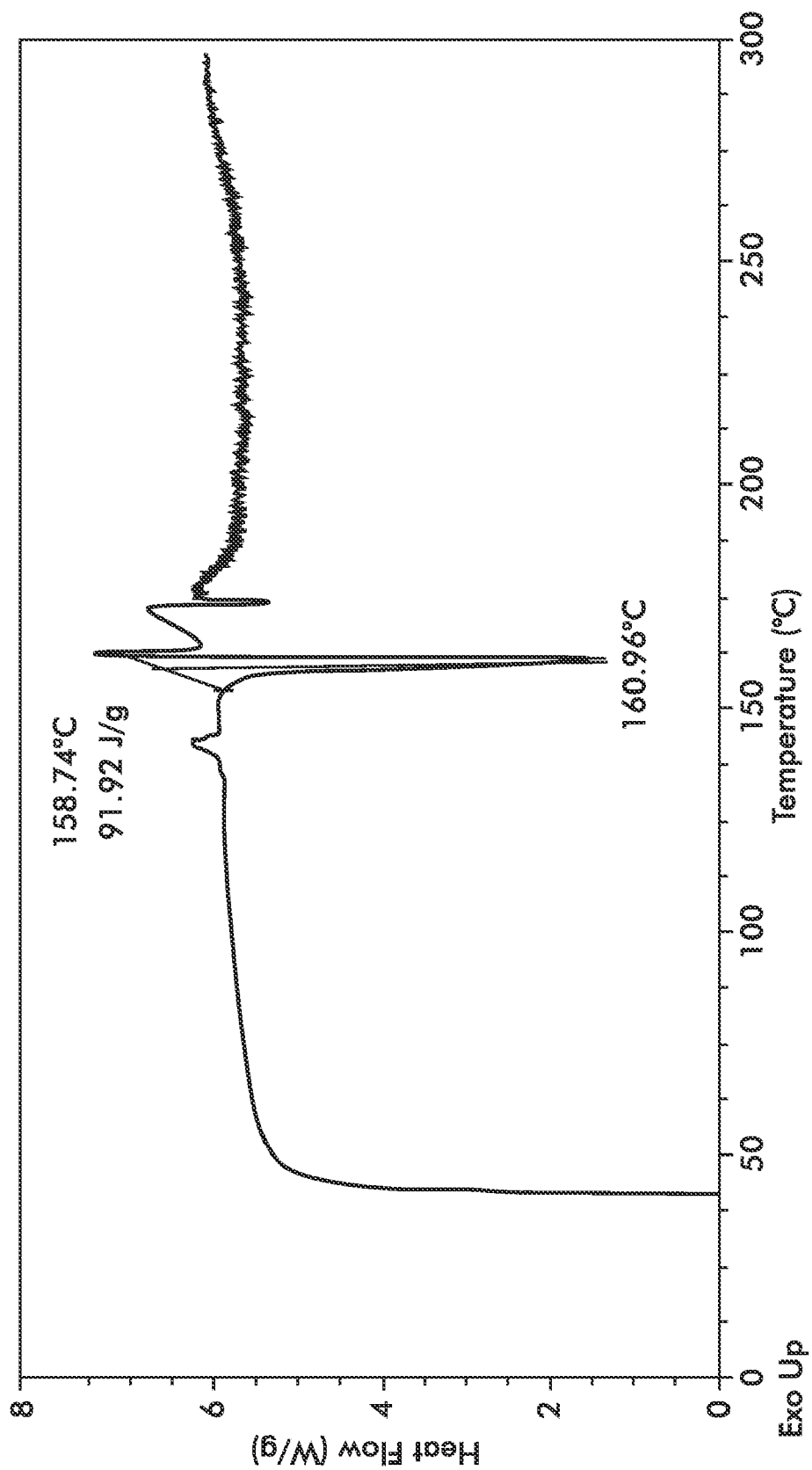
FIG. 4—DSC thermogram of a polymorph of R-(−)-modafinil (Form III).

DSC of the R-(−)-modafinil form III characterized in FIG. 4 showed an endothermic transition at about 161 degrees C.

A second batch of R-(−)-modafinil form III was prepared for further analysis via thermal microscopy and PXRD. Solubility data was also acquired. These data are discussed below.

R-(−)-modafinil Form III solubility was equal to about 6.1-7.0 mg/mL. The solubility was measured from an isopropyl acetate slurry stirred at 25 degrees C. The solubility measurement was performed via HPLC. The solid from the solubility samples were dried under nitrogen and characterized by PXRD and thermal microscopy. Form conversion was not observed during procedure.

Thermal (hotstage) microscopy was used with a heating rate of 10 degrees C./minute to measure the melting point of R-(−)-modafinil Form III, which was determined to be about 156-158 degrees C.

Figure 5:
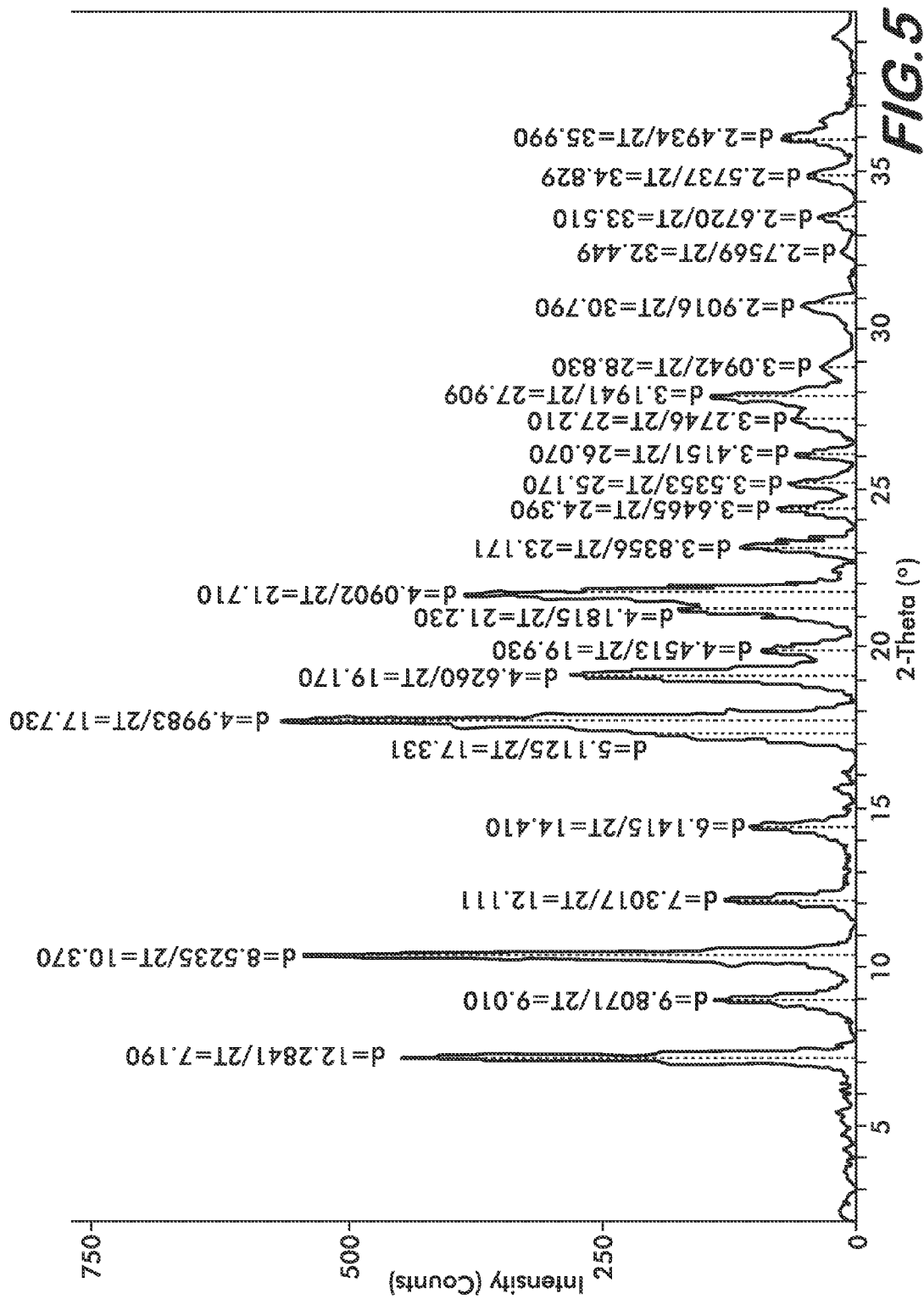
FIG. 5—PXRD diffractogram of a polymorph of R-(−)-modafinil (Form III).

R-(−)-modafinil Form III can be characterized by any one, any two, any three, any four, any five, or any six or more of the peaks in FIG. 5 including, but not limited to, 7.19, 10.37, 12.11, 14.41, 17.73, 19.17, 21.71, 23.17, 24.39, 25.17, 26.07, and 27.91 degrees 2-theta (Rigaku PXRD, data with background removed).

R-(−)-modafinil Form IV

Anhydrous ammonia gas was bubbled through a solution containing R-benzhydrylsulfinyl methyl ester (8.3 g, 0.0288 mol) in methanol (75 mL) for 10 minutes. The reaction was then stirred in a 5 degrees C. ice bath for 1 hour and ammonia gas was bubbled through for an additional 10 minutes. Stirring was continued for an additional 4 hours. After stirring for another hour a precipitate had formed (422 mg) and was collected. The filtrate was then neutralized using conc. HCl and another precipitate formed and was collected. The solid material (3 g) was passed through a column (silica gel, grade 9385, 230-400, mesh 60 angstroms), 3:1 v/v ethyl acetate and hexane as eluent). The column was then flushed with ethyl acetate (250 mL). The filtrates were combined and concentrated under reduced pressure to give R-(−)-modafinil form IV as a colorless solid (590 mg).

R-(−)-modafinil Form IV can be characterized by any one, any two, any three, any four, any five, or any six or more of the peaks in FIG. 6 including, but not limited to, 7.79, 10.31, 11.77, 16.49, 17.33, 19.47, and 23.51 degrees 2-theta (Rigaku PXRD, data as collected).

Figure 7:
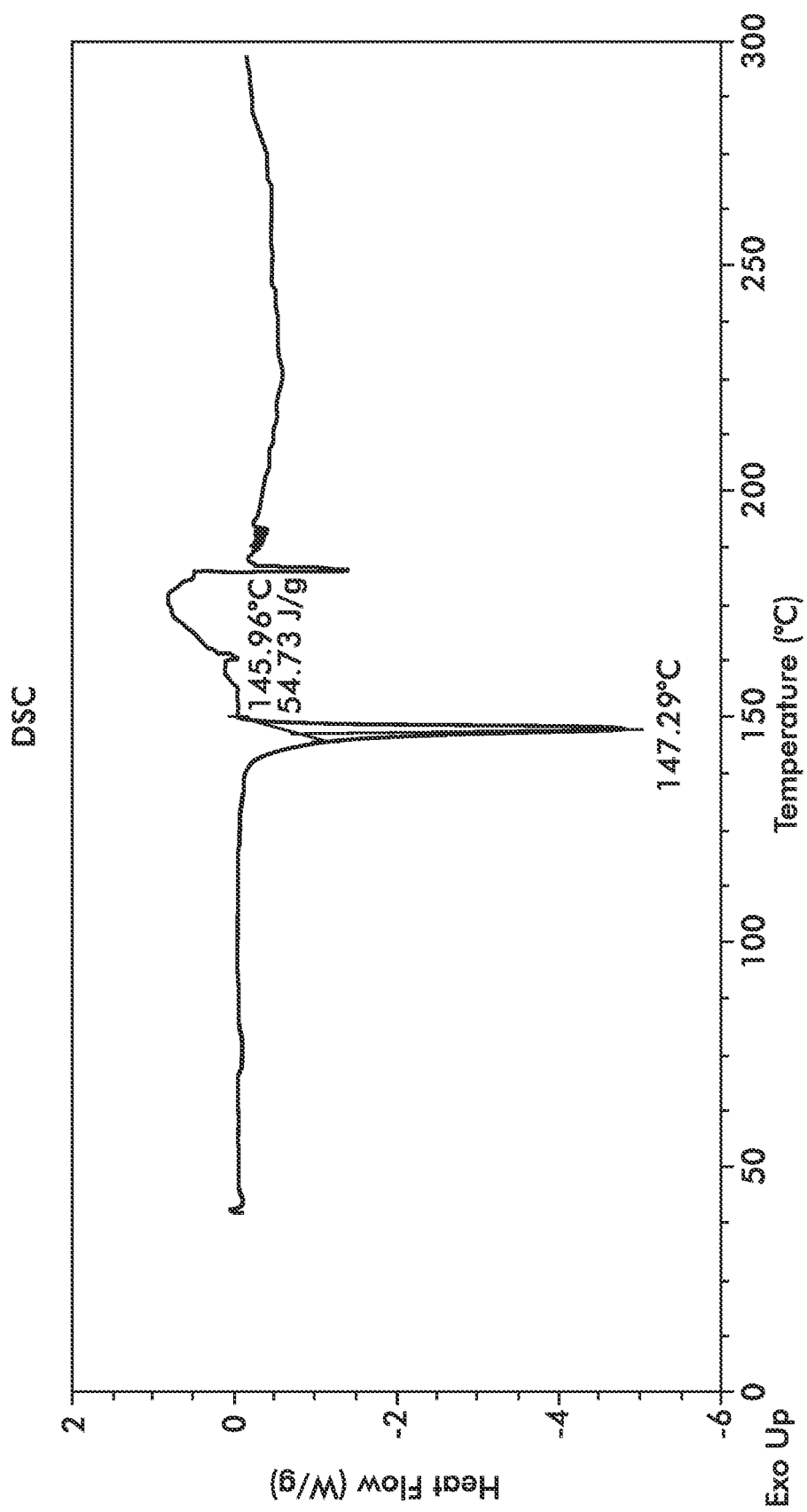
FIG. 7—DSC thermogram of a polymorph of R-(−)-modafinil (Form IV).

DSC of the R-(−)-modafinil form IV characterized in FIG. 7 showed an endothermic transition at about 147 degrees C.

A second batch of R-(−)-modafinil form IV was prepared for further analysis via thermal microscopy and PXRD. Solubility data was also acquired. These data are discussed below.

R-(−)-modafinil Form IV solubility was equal to about 3.5-4.0 mg/mL. The solubility was measured from an isopropyl acetate slurry stirred at 25 degrees C. The solubility measurement was performed via HPLC. The solid from the solubility samples were dried under nitrogen and characterized by PXRD and thermal microscopy. Form conversion was not observed during procedure.

Thermal (hotstage) microscopy was used with a heating rate of 10 degrees C./minute to measure the melting point of R-(−)-modafinil Form IV, which was determined to be about 147-158 degrees C.

Figure 8:
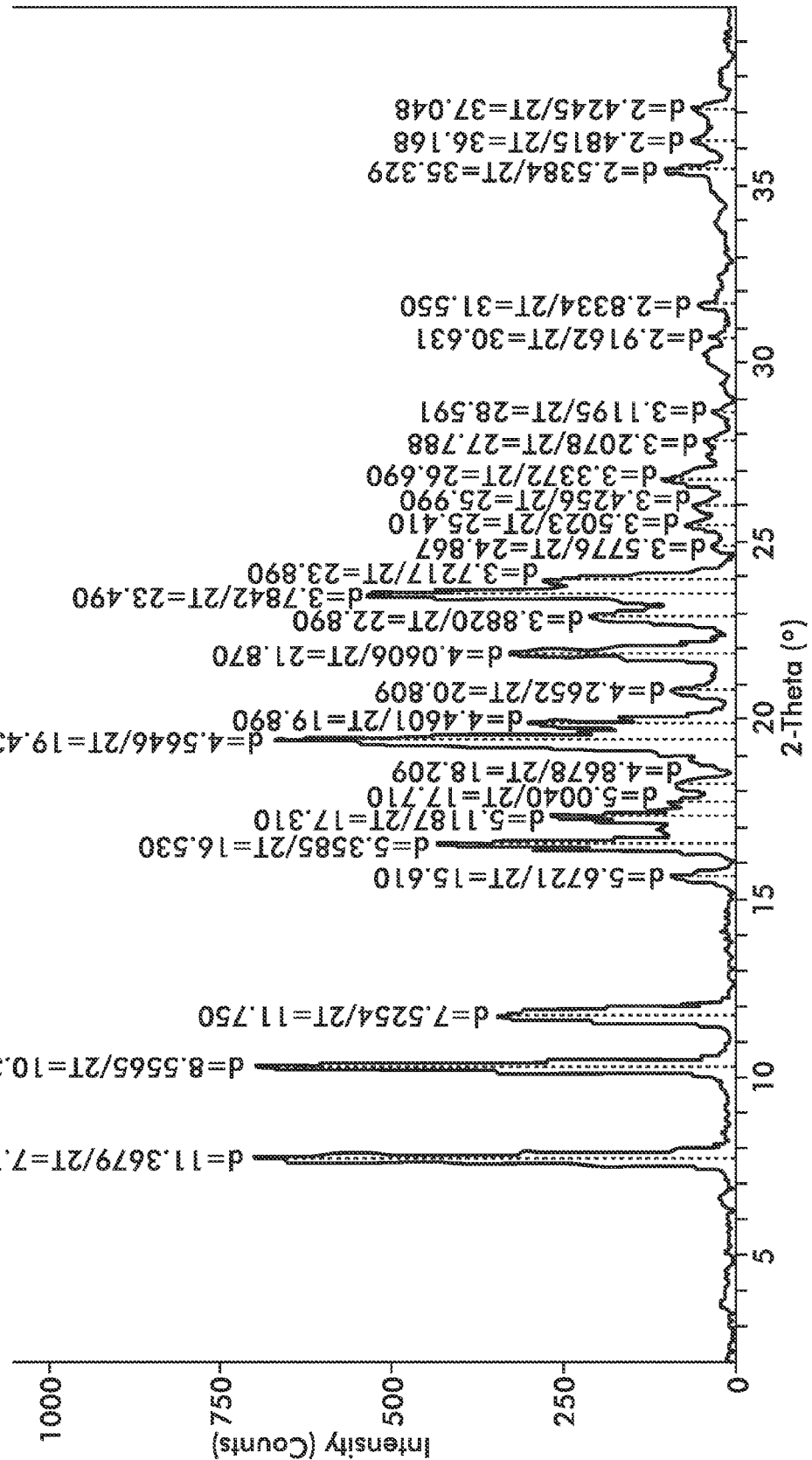
FIG. 8—PXRD diffractogram of a polymorph of R-(−)-modafinil (Form IV).

R-(−)-modafinil Form IV can be characterized by any one, any two, any three, any four, any five, or any six or more of the peaks in FIG. 8 including, but not limited to, 7.77, 10.33, 11.75, 16.53, 19.43, 19.89, 21.87, 23.49, and 26.69 degrees 2-theta (Rigaku PXRD, data with background removed).

R-(−)-modafinil Form V

R-(−)-modafinil form IV (prepared in procedure above) was heated in a solution of ethanol until the mixture was boiling and then was cooled to room temperature. The solid material was then collected and characterized as R-(−)-modafinil form V.

R-(−)-modafinil Form V can be characterized by any one, any two, any three, any four, any five, or any six or more of the peaks in FIG. 9 including, but not limited to, 6.61, 10.39, 13.99, 16.49, 17.73, 19.03, 20.87, 22.31, and 25.99 degrees 2-theta (Rigaku PXRD, data as collected).

A second batch of R-(−)-modafinil form V was prepared for further analysis via thermal microscopy and PXRD. Solubility data was also acquired. These data are discussed below.

R-(−)-modafinil Form V solubility was equal to about 2.1-2.6 mg/mL. The solubility was measured from an isopropyl acetate slurry stirred at 25 degrees C. The solubility measurement was performed via HPLC. The solid from the solubility samples were dried under nitrogen and characterized by PXRD and thermal microscopy. Form conversion was not observed during procedure.

Thermal (hotstage) microscopy was used with a heating rate of 10 degrees C./minute to measure the melting point of R-(−)-modafinil form V, which was determined to be about 159 degrees C.

Figure 10:
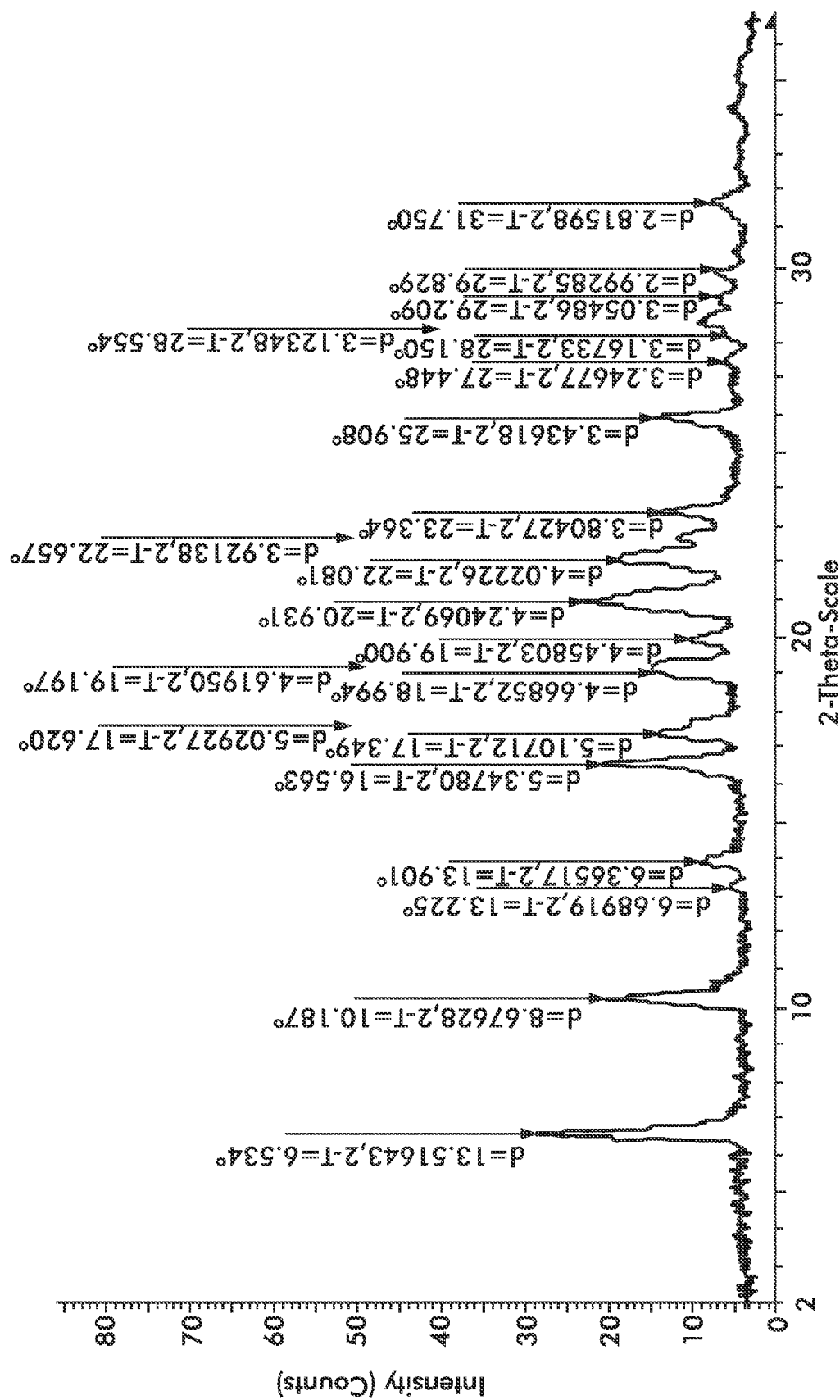
FIG. 10—PXRD diffractogram of a polymorph of R-(−)-modafinil (Form V).

R-(−)-modafinil Form V can be characterized by any one, any two, any three, any four, any five, or any six or more of the peaks in FIG. 10 including, but not limited to, 6.53, 10.19, 13.90, 16.56, 17.35, 17.62, 18.99, 20.93, 22.08, 23.36, and 25.91 degrees 2-theta (Bruker PXRD, data as collected).

The polymorphs of R-(−)-modafinil are named Forms III, IV, and V based on similarities in the PXRD diffractograms to those found in the diffractograms for corresponding racemic modafinil Forms III, IV, and V in US Patent Application No. 20020043207, published on Apr. 18, 2002.

Example 3

2:1 R-(−)-modafinil:S-(+)-modafinil

A solution containing R-(−)-modafinil (80.16 mg, 0.293 mmol) and racemic modafinil (20.04 mg, 0.0366 mmol) in ethanol (2 mL) was prepared. The mixture was heated to boiling in order to dissolve the entire solid and was then cooled to room temperature (25 degrees C.). After remaining at room temperature for 15 minutes, the solution was placed at 5 degrees C. overnight. The solution was then decanted and the remaining crystals were dried under a flow of nitrogen gas and characterized using HPLC, PXRD, DSC, and thermal microscopy.

The crystals obtained contained between about 63 and about 67 percent R-(−)-modafinil and the remainder of the crystals was S-(+)-modafinil. HPLC analysis indicated that the crystals were a 2:1 phase containing two R-(−)-modafinil molecules for every one S-(+)-modafinil molecule.

Figure 11:
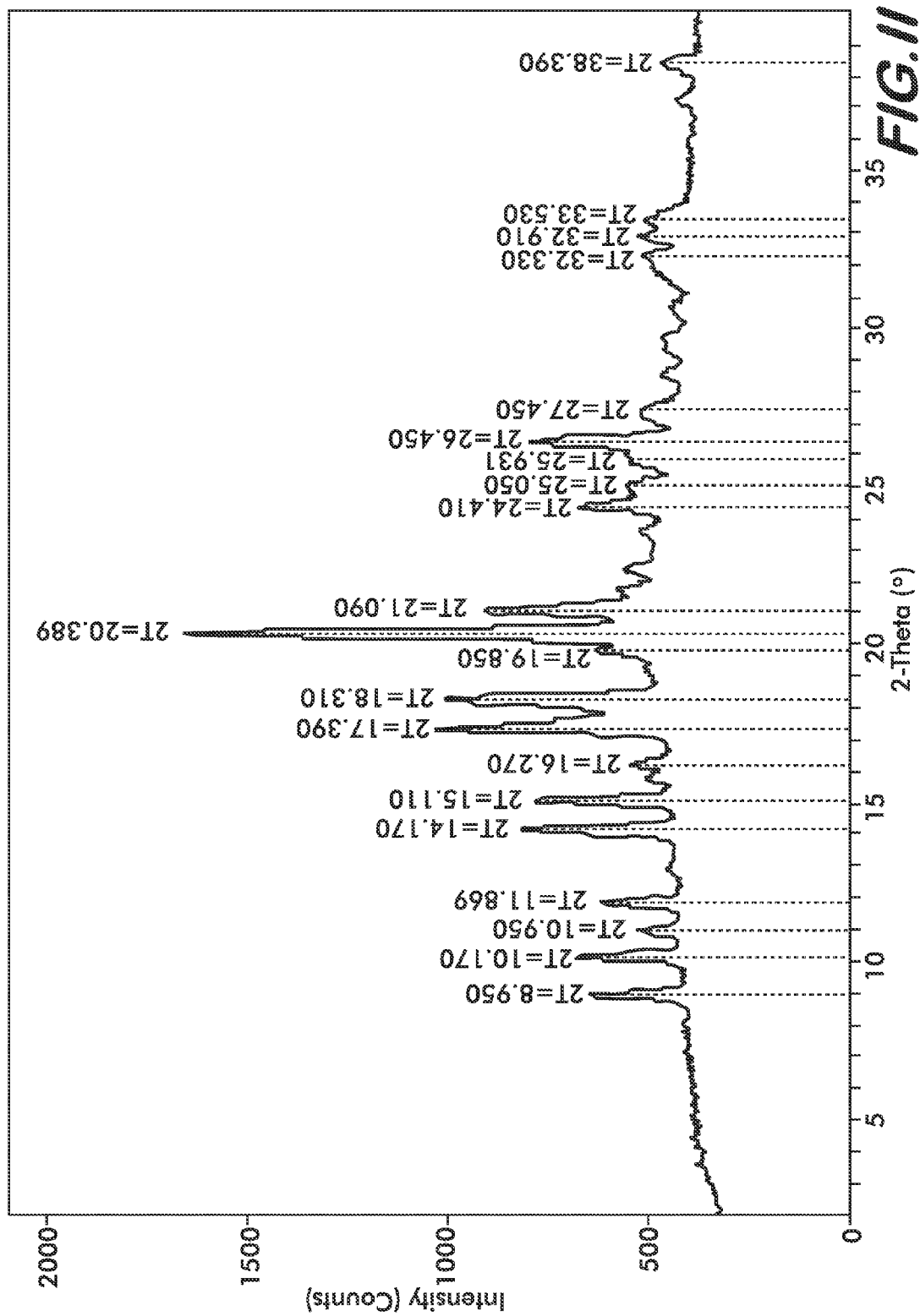
FIG. 11—PXRD diffractogram of 2:1 R-(−)-modafinil:S-(+)-modafinil.

PXRD was completed on a single crystal sample of the 2:1 R-(−)-modafinil:S-(+)-modafinil. 2:1 R-(−)-modafinil:S-(+)-modafinil can be characterized by any one, any two, any three, any four, any five, or any six or more of the peaks in FIG. 11 including, but not limited to, 8.95, 10.17, 11.87, 14.17, 15.11, 17.39, 18.31, 20.39, 21.09, 24.41, and 26.45 degrees 2-theta (Rigaku PXRD, data as collected).

Figure 12:
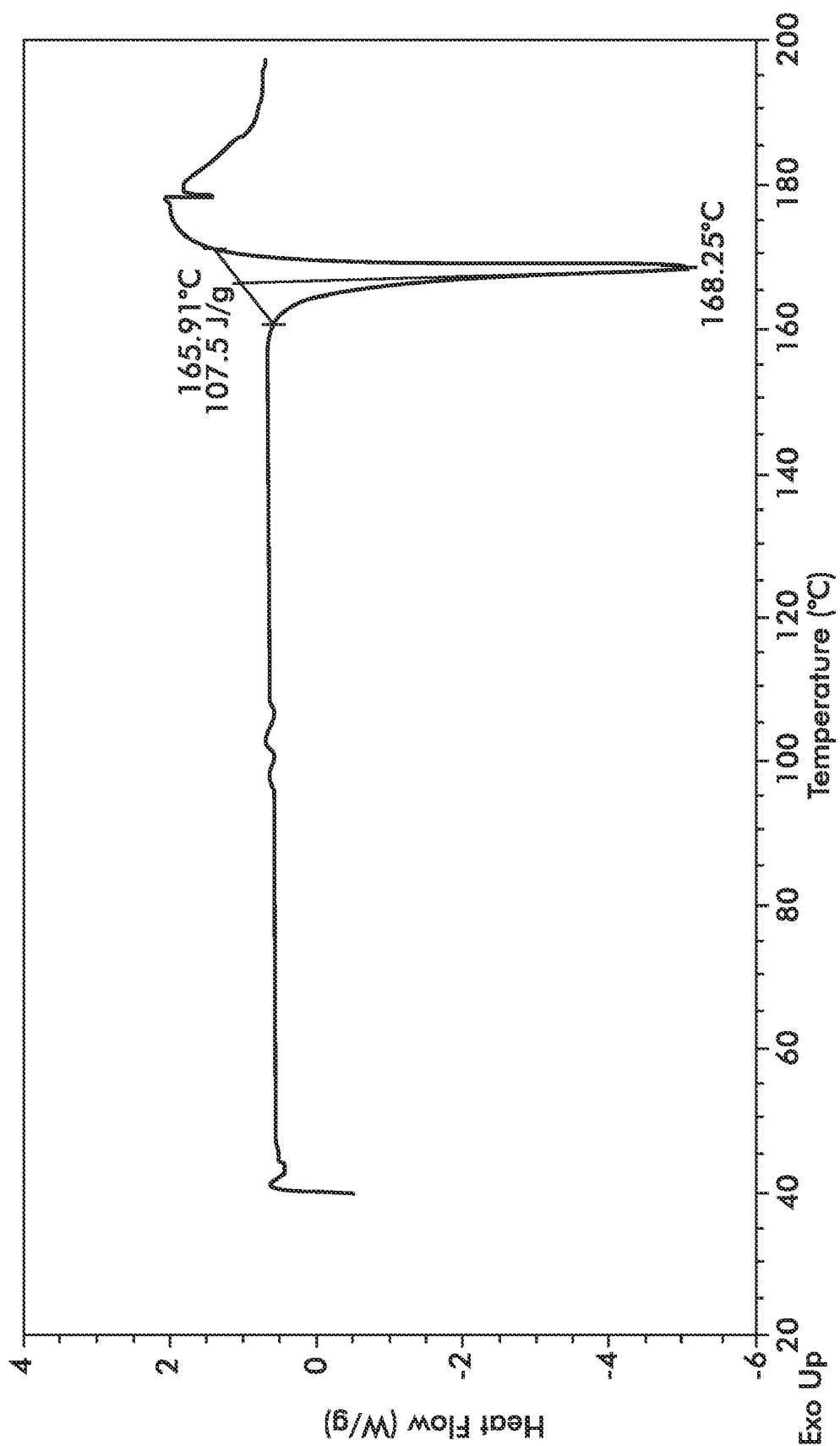
FIG. 12—DSC thermogram of 2:1 R-(−)-modafinil:S-(+)-modafinil.

DSC of the 2:1 R-(−)-modafinil:S-(+)-modafinil characterized in FIG. 12 showed an endothermic transition at about 168 degrees C.

Thermal (hotstage) microscopy was used with a heating rate of 5 degrees C/minute to measure the melting point of 2:1 R-(−)-modafinil:S-(+)-modafinil, which was determined to be about 160-166 degrees C.

Example 4

R-(−)-modafinil Form IV 105.9 mg of R-(−)-modafinil was slurried in 1.5 mL of ethanol for 2 days. The liquor was filtered off and then dried under flowing nitrogen gas. The resultant solid was analyzed via PXRD and was determined to be R-(−)-modafinil form IV (FIG. 13).

Figure 13:
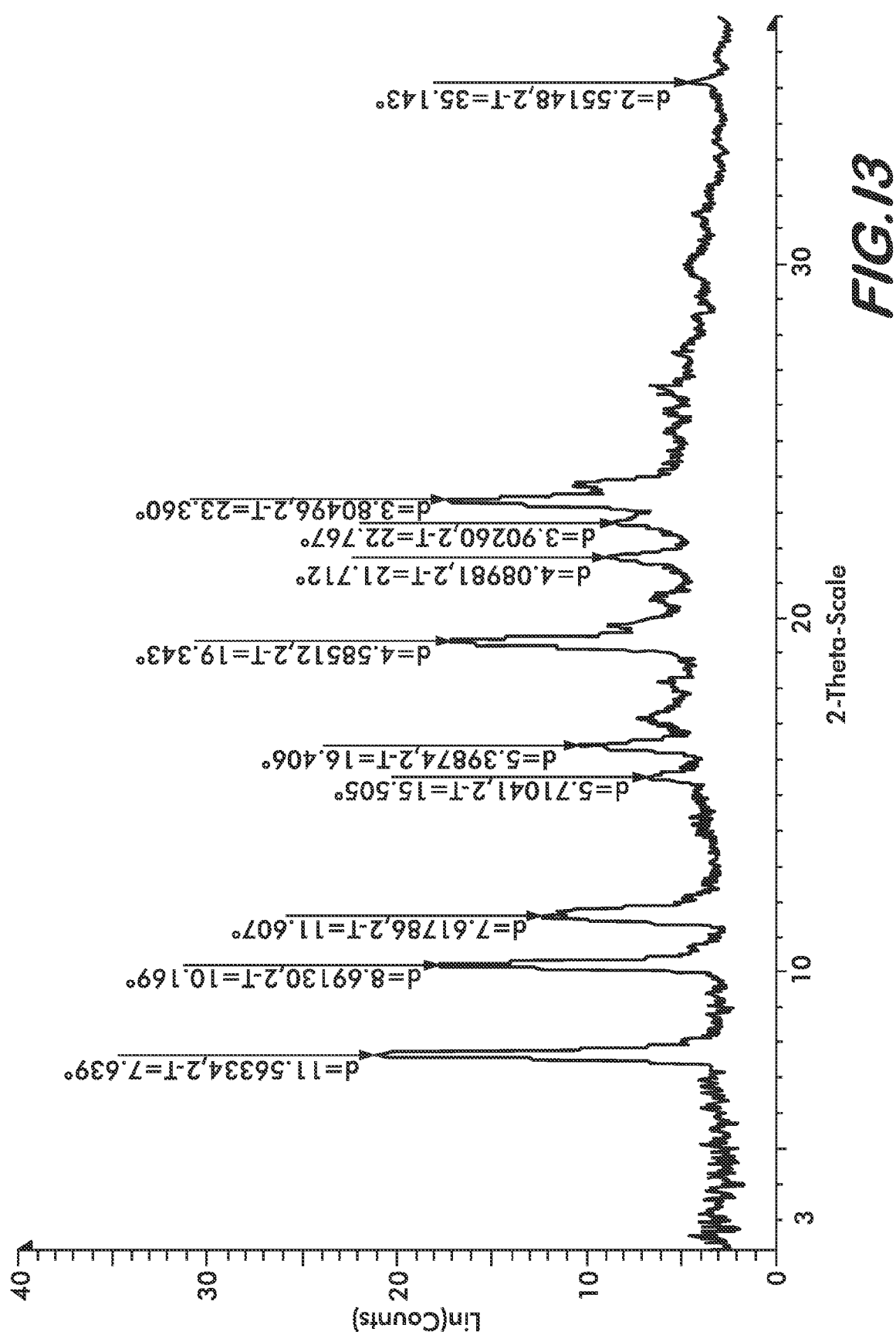
FIG. 13—PXRD diffractogram of R-(−)-modafinil form IV.

R-(−)-modafinil Form IV can be characterized by any one, any two, any three, any four, any five, or any six or more of the peaks in FIG. 13 including, but not limited to, 7.64, 10.17, 11.61, 16.41, 19.34, 21.71, 22.77, and 23.36 degrees 2-theta (Bruker PXRD, data as collected).

R-(−)-modafinil form IV was also recovered via thermal recrystallization from ethanol and via the slow evaporation of solvent from ethanol.

Example 5

R-(−)-modafinil Form V 107.7 mg of R-(−)-modafinil was dispensed into 3 mL ethyl acetate. The suspension was heated on a hotplate (60 degrees C.) to dissolve the solid. Approximately one third to one half of the heated solvent was evaporated off with flowing nitrogen gas. The mixture was then cooled to room temperature (25 degrees C.). A centrifuge filter was used to separate the solid from the liquid. The resultant solid was analyzed via PXRD and DSC and was determined to be R-(−)-modafinil form V (FIGS. 14 and 15).

Figure 14:
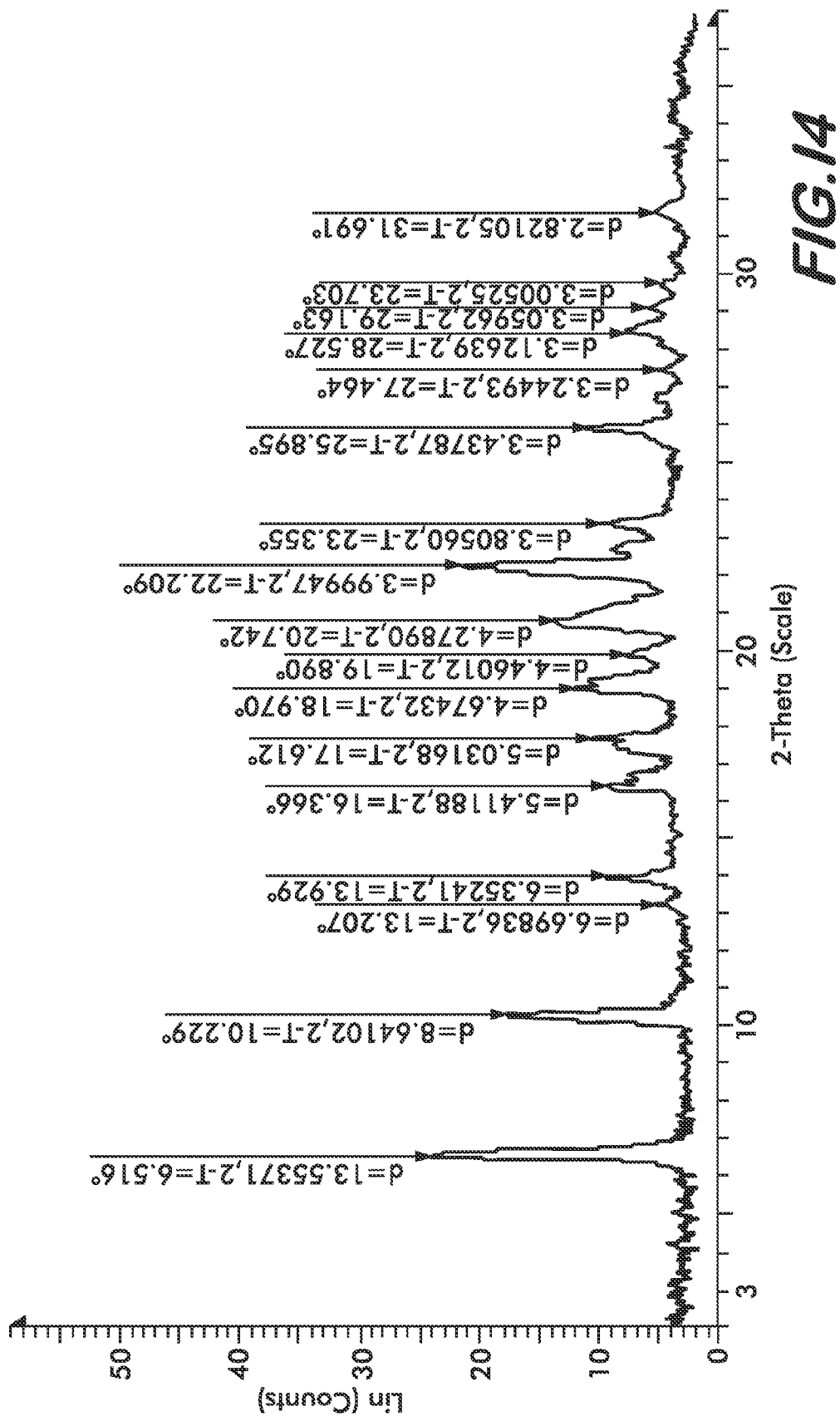
FIG. 14—PXRD diffractogram of R-(−)-modafinil form V.
Figure 15:
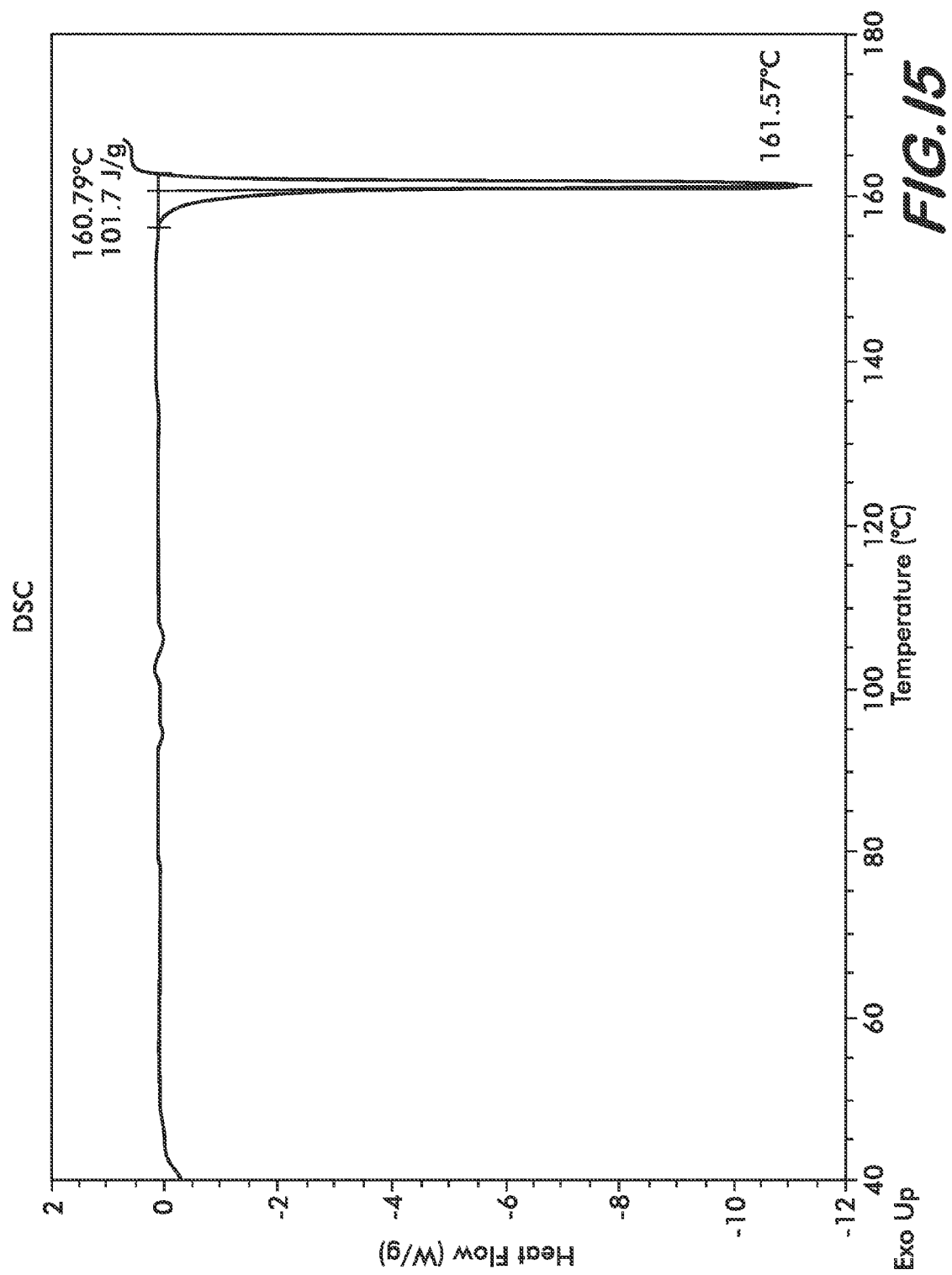
FIG. 15—DSC thermogram of R-(−)-modafinil form V.

R-(−)-modafinil Form V can be characterized by any one, any two, any three, any four, any five, or any six or more of the peaks in FIG. 14 including, but not limited to, 6.52, 10.23, 13.93, 16.37, 17.61, 18.97, 20.74, 22.21, 23.36, and 25.90 degrees 2-theta (Bruker PXRD, data as collected).

DSC of the R-(−)-modafinil form V was completed. FIG. 15 showed an endothermic transition at about 161-162 (161.57) degrees C.

Example 6

R-(−)-modafinil Chloroform Solvate 200 microliters chloroform was added to 30.5 mg R-(−)-modafinil. Mixture was heated at 75 degrees C. for 30 minutes, and then an additional 200 microliters chloroform was added. After an additional 30 minutes, the solid had completely dissolved. The sample was heated for an additional 2 hours. After heating, the sample was cooled to 5 degrees C. at a rate of about 1 degree/minute. Upon reaching 5 degrees C., the sample was still a homogeneous liquid solution. The sample was then placed under nitrogen flow for one minute causing crystals to begin to form. Sample was again incubated at 5 degrees C. and more solid crashed out. The sample was then dried under nitrogen flow and characterized by PXRD and TGA.

Figure 16:
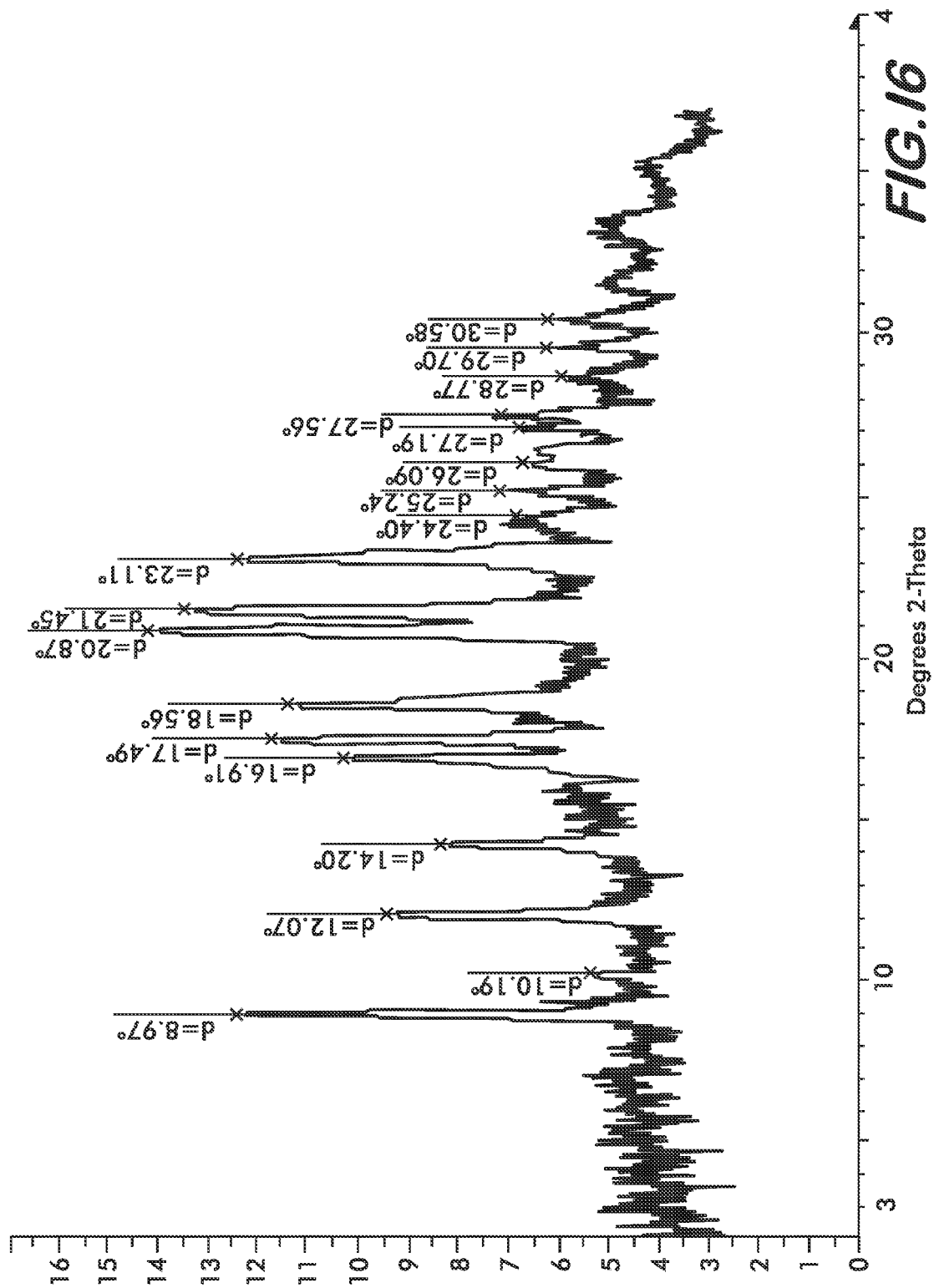
FIG. 16—PXRD diffractogram of R-(−)-modafinil chloroform solvate.

PXRD was completed on the R-(−)-modafinil chloroform solvate. R-(−)-modafinil chloroform solvate can be characterized by any one, any two, any three, any four, any five, or any six or more of the peaks in FIG. 16 including, but not limited to, 8.97, 12.07, 14.20, 16.91, 17.49, 18.56, 20.87, 21.45, 23.11, and 25.24 degrees 2-theta (Bruker PXRD, data as collected).

Figure 17:
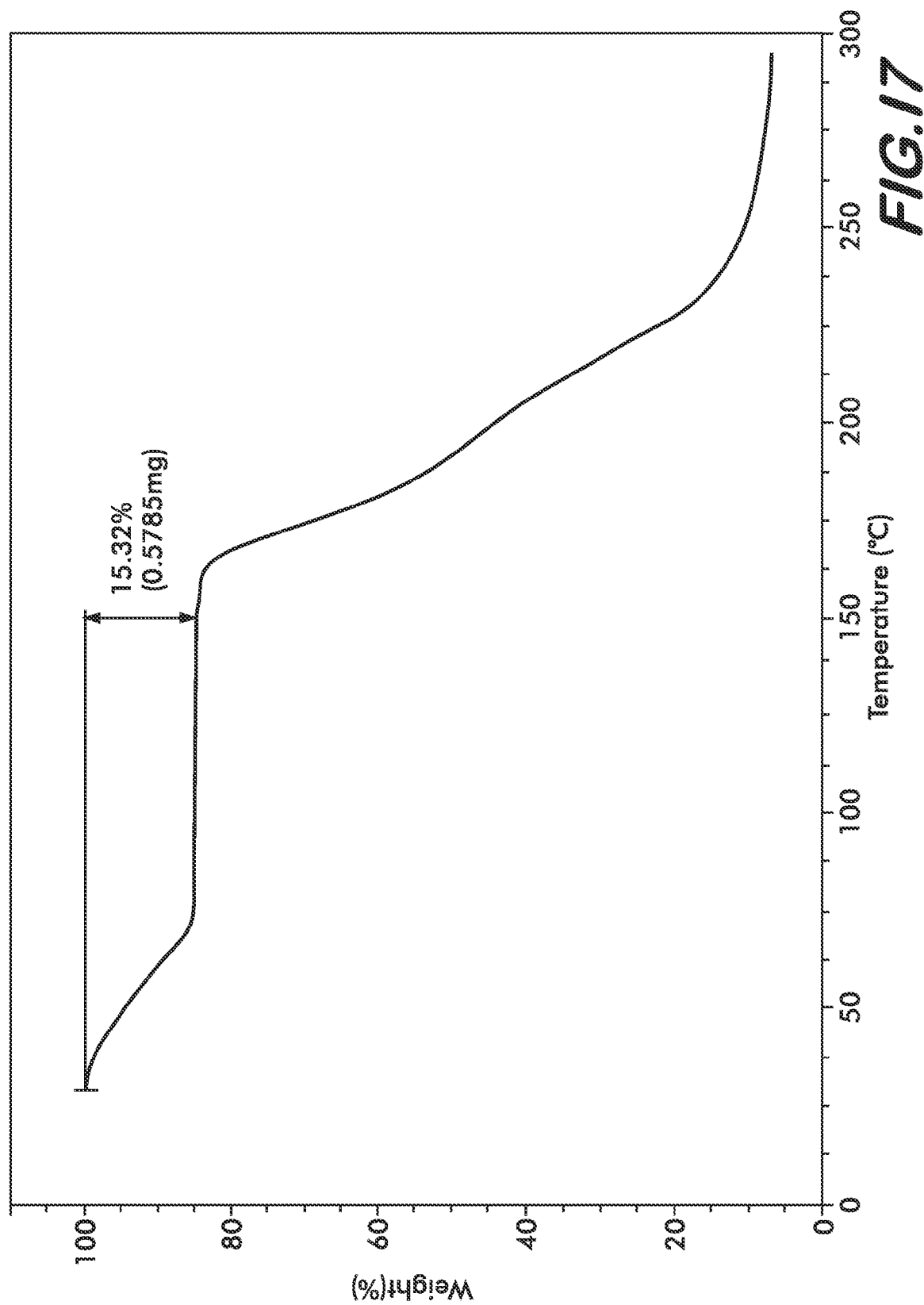
FIG. 17—TGA thermogram of R-(−)-modafinil chloroform solvate.

TGA of the R-(−)-modafinil chloroform solvate was completed. FIG. 17 showed about a 15 percent weight loss between about 25 and about 150 degrees C.

Example 7

R-(−)-modafinil Chlorobenzene Solvate

R-(−)-modafinil (102.6 mg, 0.375 mmol) was suspended in chlorobenzene (5 mL) and heated on a 60 degrees C. hotplate. The mixture was allowed to cool to about 25 degrees C. The slurry was then reheated and THF was added until all solids were dissolved. The solution was then allowed to cool while being stored at room temperature for 4 days in a sealed vial. After storage, the resultant solid was collected via vacuum filtration and characterized via PXRD.

Figure 18:
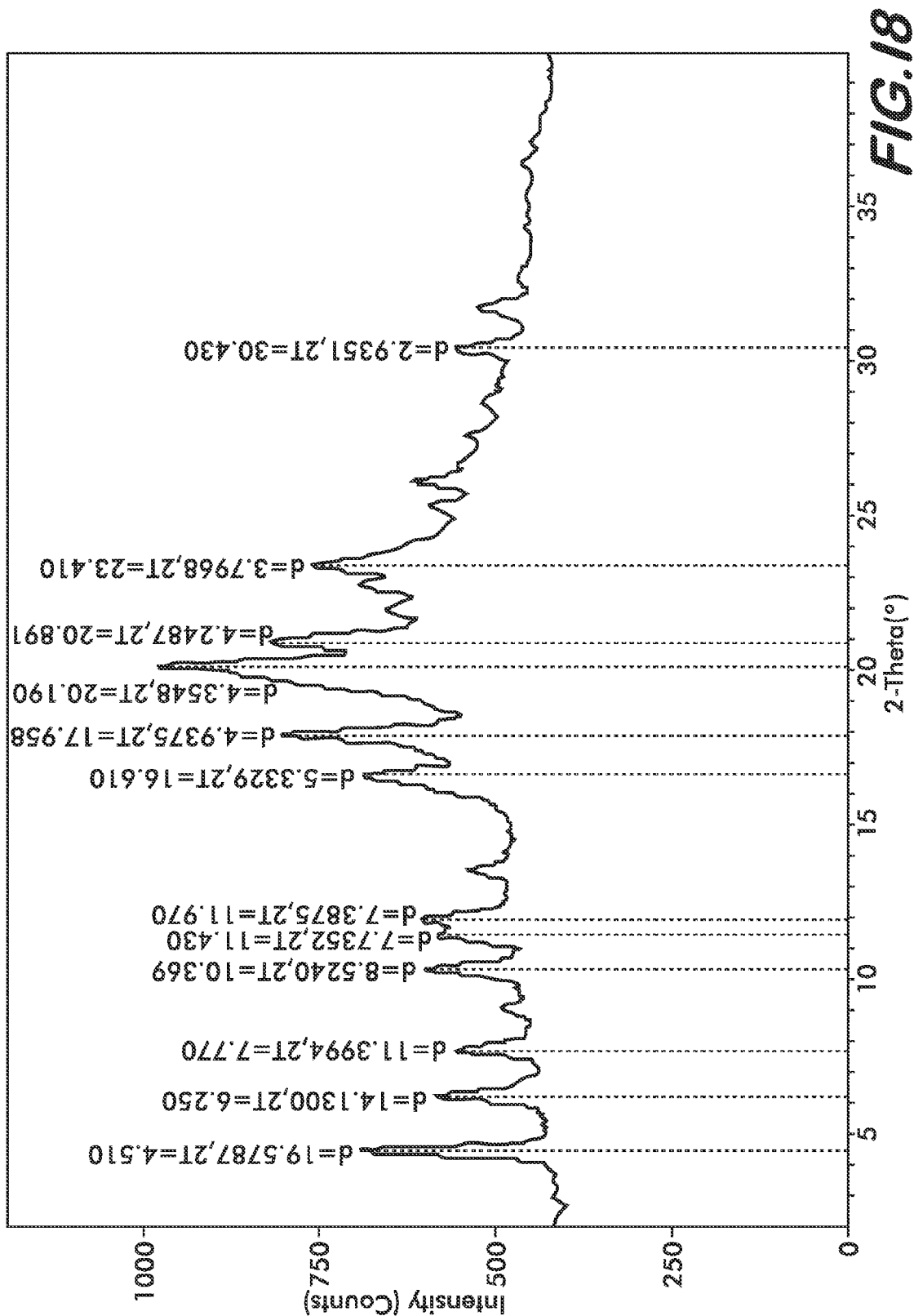
FIG. 18—PXRD diffractogram of R-(−)-modafinil chlorobenzene solvate.

PXRD was completed on the R-(−)-modafinil chlorobenzene solvate. R-(−)-modafinil chlorobenzene solvate can be characterized by any one, any two, any three, any four, any five, or any six or more of the peaks in FIG. 18 including, but not limited to, 4.51, 6.25, 7.77, 10.37, 11.43, 11.97, 16.61, 17.95, 20.19, 20.89, 23.41, and 30.43 degrees 2-theta (Rigaku PXRD, data as collected).

Example 8

Ethyl Acetate Channel Solvate of Racemic Modafinil

The ethyl acetate channel solvate of racemic modafinil was made from a solution of racemic modafinil (53.7 mg, 0.196 mmol) and 1-hydroxy-2-naphthoic acid (75.5 mg, 0.401 mmol) in 2.4 mL of ethyl acetate, dissolved over a 60 degrees C. hotplate. Once cooled, the solution was seeded with ground co-crystals of R-(−)-modafinil:1-hydroxy-2-naphthoic acid (see Example 17 of Application No. PCT/US2004/29013).

Figure 19:
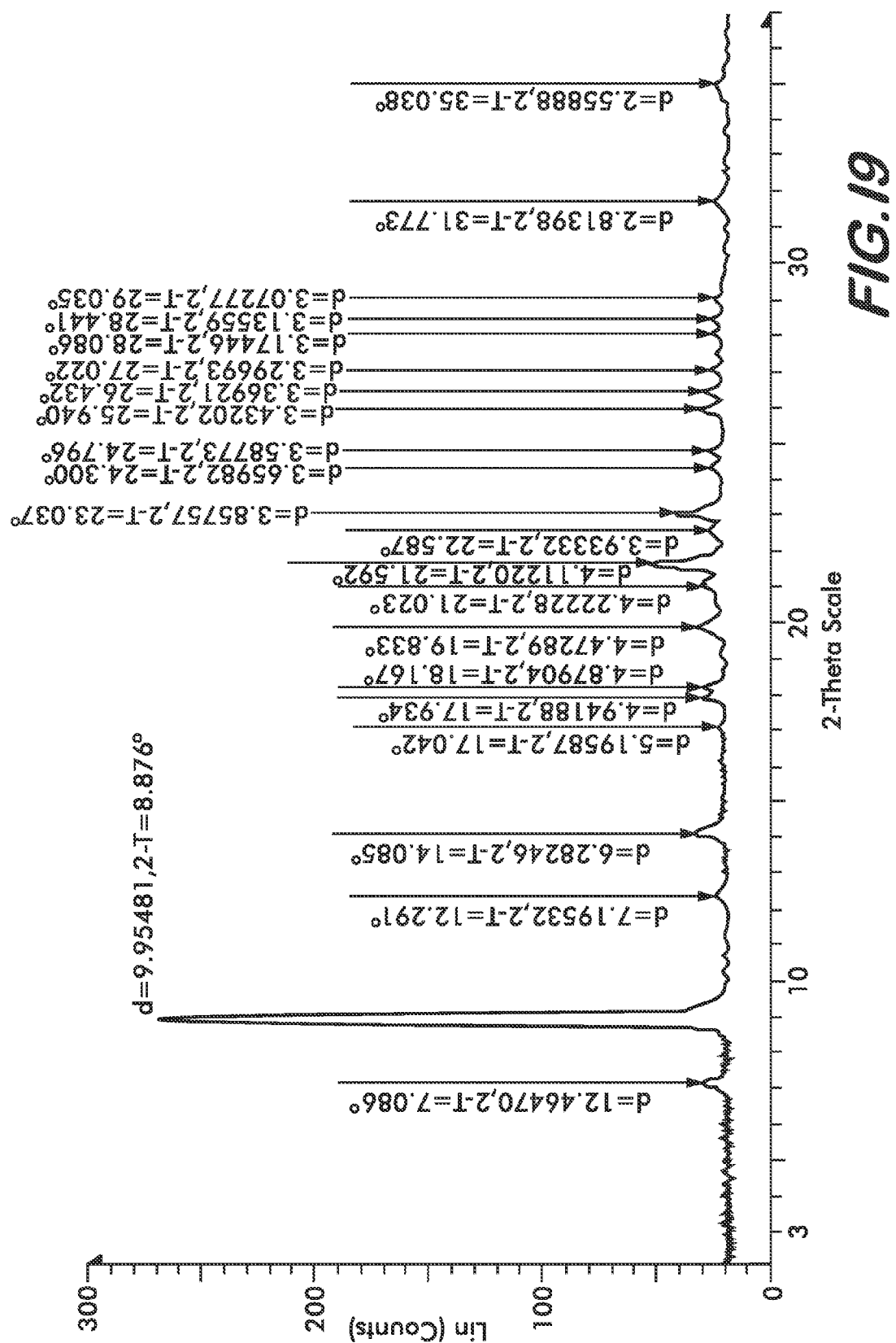
FIG. 19—PXRD diffractogram of racemic modafinil ethyl acetate channel solvate.

PXRD was completed on the ethyl acetate channel solvate of racemic modafinil. The ethyl acetate channel solvate of racemic modafinil can be characterized by any one, any two, any three, any four, any five, or any six or more of the peaks in FIG. 19 including, but not limited to, 8.88, 14.09, 19.83, 21.59, 23.04, and 25.94 degrees 2-theta (Bruker PXRD, data as collected).

Figure 20:
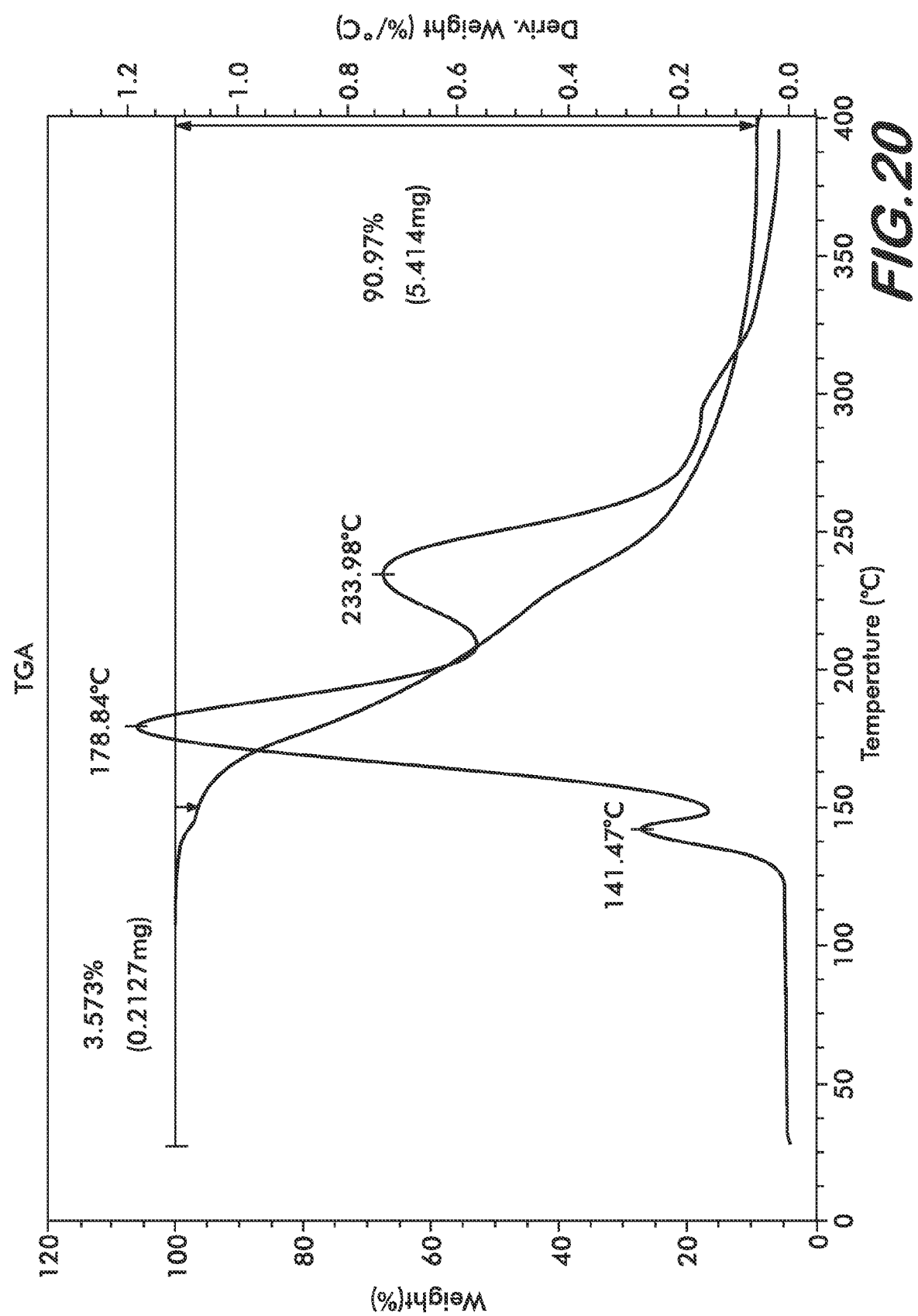
FIG. 20—TGA thermogram of racemic modafinil ethyl acetate channel solvate.

TGA of the ethyl acetate channel solvate of racemic modafinil was completed. FIG. 20 showed about a 3.6 percent weight loss between about 25 and about 150 degrees C.

Example 9

R-(−)-modafinil Acetic Acid Solvate

The R-(−)-modafinil acetic acid solvate was formed by grinding R-(−)-modafinil (105.5 mg) in 0.066 mL of acetic acid for 10 minutes in stainless steel cylinder with a Wig-L-Bug grinder/mixer. The powder was then analyzed by DSC, TGA, and PXRD.

Figure 21:
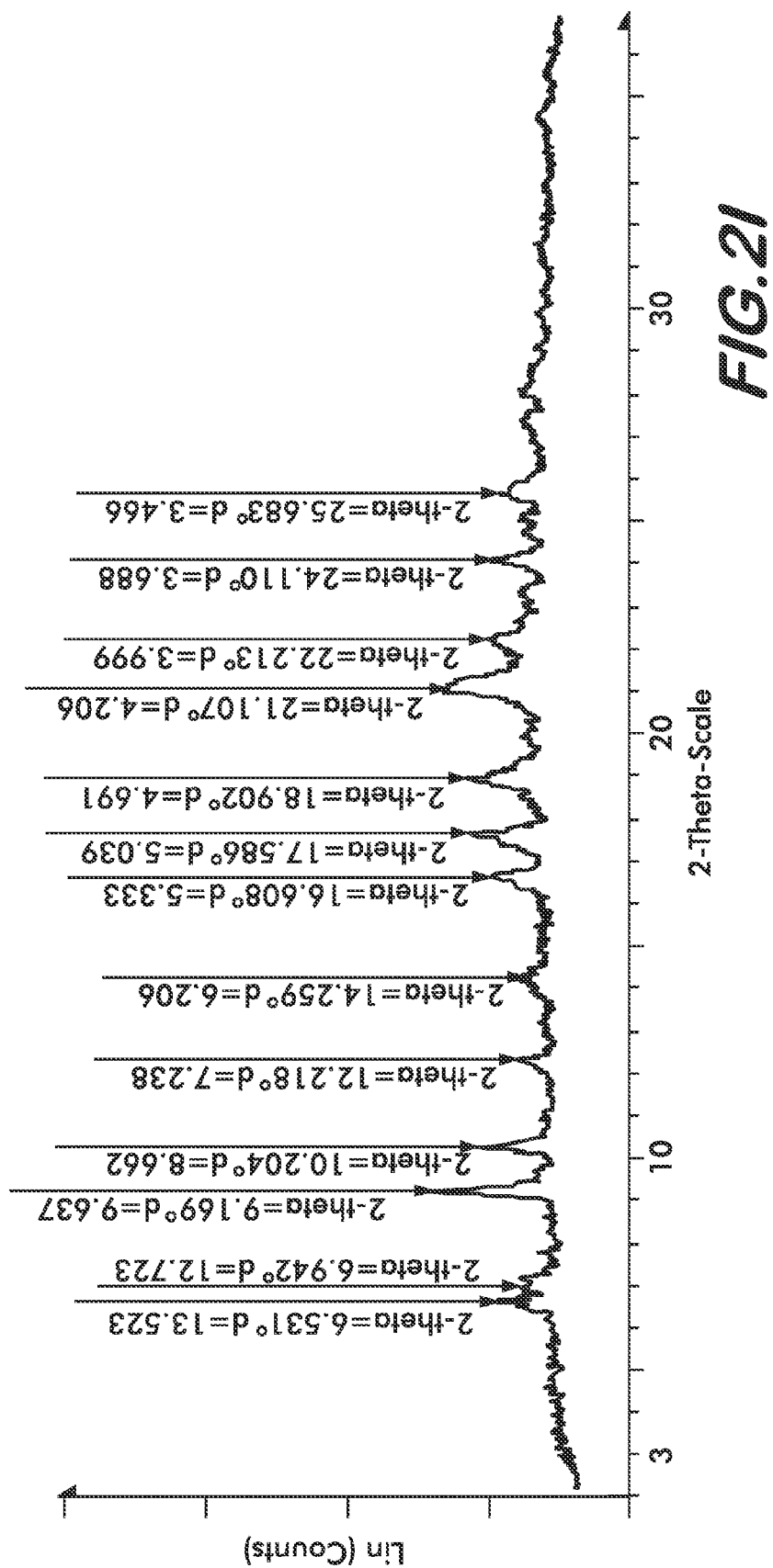
FIG. 21—PXRD diffractogram of R-(−)-modafinil acetic acid solvate.

PXRD was completed on the R-(−)-modafinil acetic acid solvate. The solvate can be characterized by any one, any two, any three, any four, any five, or any six or more of the peaks in FIG. 21 including, but not limited to, 9.17, 10.20, 16.61, 17.59, 18.90, 21.11, and 24.11 degrees 2-theta (Bruker PXRD, data as collected).

Figure 22:
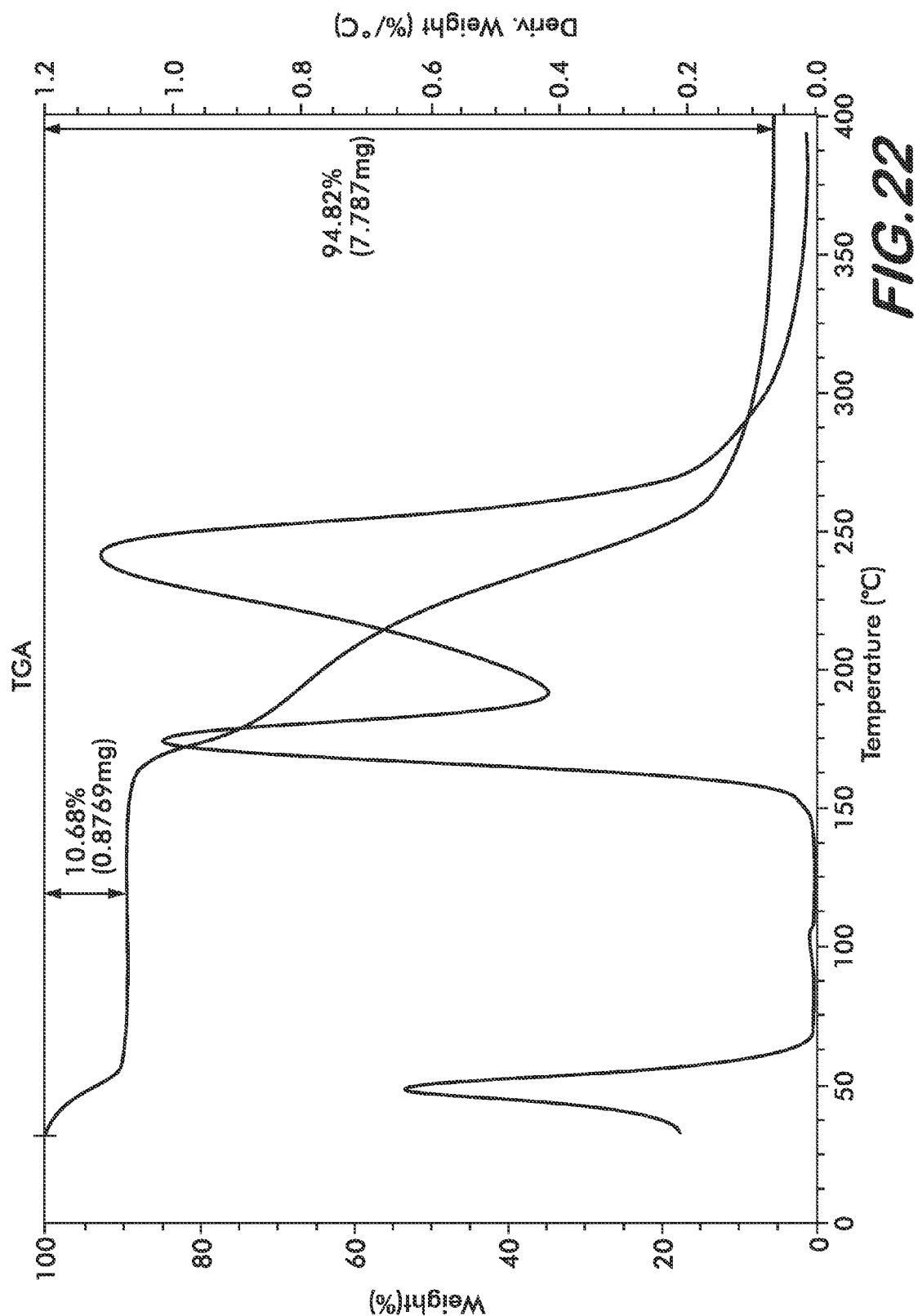
FIG. 22—TGA thermogram of R-(−)-modafinil acetic acid solvate.

TGA of the R-(−)-modafinil acetic acid solvate was completed. FIG. 22 showed about an 11 percent weight loss between about 25 and about 125 degrees C.

Figure 23:
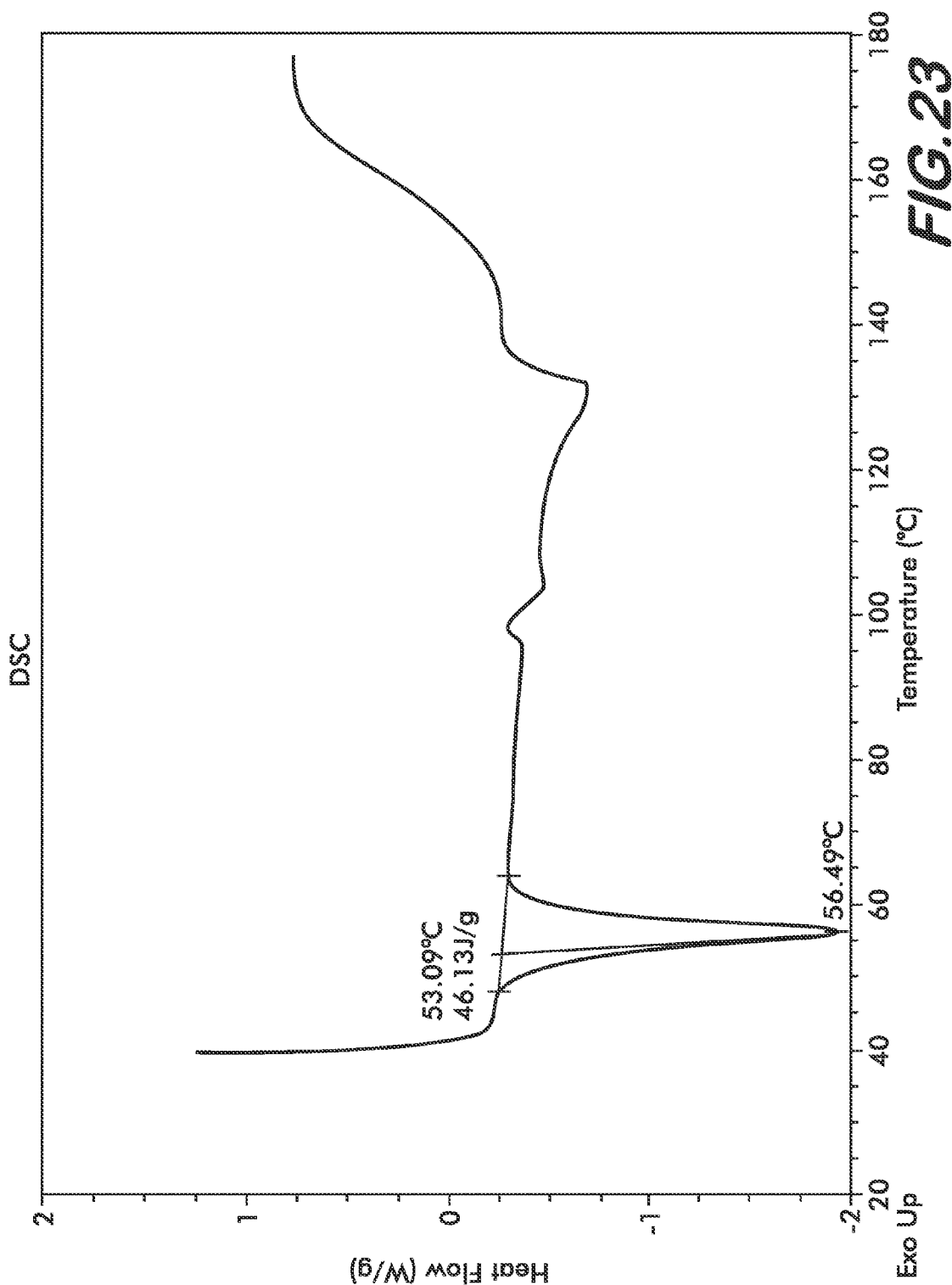
FIG. 23—DSC thermogram of R-(−)-modafinil acetic acid solvate.

DSC of the R-(−)-modafinil acetic acid solvate was completed. FIG. 23 showed an endothermic transition at about 56 degrees C.

What is claimed is:

1. A solvate of R-(−)-modafinil, wherein the solvent molecule is selected from the group consisting of: chloroform, chlorobenzene, and acetic acid.

2. The solvate of claim 1, wherein the solvate is characterized by a powder X-ray diffraction pattern comprising peaks expressed in terms of 2-theta angles, wherein:
   (a) said solvate is a chloroform solvate and said X-ray diffraction pattern comprises peaks at 8.97, 12.07, and 14.20 degrees;
   (b) said solvate is a chloroform solvate and said X-ray diffraction pattern comprises peaks at 17.49, 18.56, and 20.87 degrees;
   (c) said solvate is a chloroform solvate and said X-ray diffraction pattern comprises peaks at 8.97 and 12.07 degrees;
   (d) said solvate is a chloroform solvate and said X-ray diffraction pattern comprises peaks at 20.87 and 23.11 degrees; or
   (e) said solvate is a chloroform solvate and said X-ray diffraction pattern comprises a peak at 8.97 degrees.

3. The solvate of claim 1, wherein the solvate is characterized by a powder X-ray diffraction pattern comprising peaks expressed in terms of 2-theta angles, wherein:
   (a) said solvate is a chlorobenzene solvate and said X-ray diffraction pattern comprises peaks at 4.51, 6.25, and 7.77 degrees;
   (b) said solvate is a chlorobenzene solvate and said X-ray diffraction pattern comprises peaks at 10.37, 16.61, and 17.95 degrees;
   (c) said solvate is a chlorobenzene solvate and said X-ray diffraction pattern comprises peaks at 4.51 and 7.77 degrees;
   (d) said solvate is a chlorobenzene solvate and said X-ray diffraction pattern comprises peaks at 10.37 and 17.95 degrees; or
   (e) said solvate is a chlorobenzene solvate and said X-ray diffraction pattern comprises a peak at 4.51 degrees.

4. The solvate of claim 1, wherein the solvate is characterized by a powder X-ray diffraction pattern comprising peaks expressed in terms of 2-theta angles, wherein:
   (a) said solvate is an acetic acid solvate and said X-ray diffraction pattern comprises peaks at 9.17, 10.20, and 16.61 degrees;
   (b) said solvate is an acetic acid solvate and said X-ray diffraction pattern comprises peaks at 6.53, 6.94, and 17.59 degrees;
   (c) said solvate is an acetic acid solvate and said X-ray diffraction pattern comprises peaks at 9.17 and 10.20 degrees;
   (d) said solvate is an acetic acid solvate and said X-ray diffraction pattern comprises peaks at 16.61 and 17.59 degrees; or
   (e) said solvate is an acetic acid solvate and said X-ray diffraction pattern comprises a peak at 9.17 degrees.

* * * * *